(12) United States Patent
Gelbart et al.

(10) Patent No.: US 8,758,386 B2
(45) Date of Patent: Jun. 24, 2014

(54) IN VIVO INFLATABLE STRUCTURES, FOR EXAMPLE TO EXPAND STENTS

(76) Inventors: Daniel Gelbart, Vancouver (CA); Matthew J. Rust, North Vancouver (CA)

( * ) Notice: Subject to any disclaimer, the term of this patent is extended or adjusted under 35 U.S.C. 154(b) by 990 days.

(21) Appl. No.: 13/127,977

(22) PCT Filed: Nov. 6, 2008

(86) PCT No.: PCT/US2008/082700
§ 371 (c)(1),
(2), (4) Date: May 12, 2011

(87) PCT Pub. No.: WO2009/061969
PCT Pub. Date: May 14, 2009

(65) Prior Publication Data
US 2011/0238105 A1   Sep. 29, 2011

Related U.S. Application Data

(60) Provisional application No. 61/030,173, filed on Feb. 20, 2008, provisional application No. 60/985,858, filed on Nov. 6, 2007.

(51) Int. Cl.
*A61M 29/00* (2006.01)

(52) U.S. Cl.
USPC ........................................................ 606/192

(58) Field of Classification Search
USPC ........ 606/191, 194, 198; 623/1.11, 1.23, 2.11
See application file for complete search history.

(56) References Cited

U.S. PATENT DOCUMENTS

| | | | |
|---|---|---|---|
| 3,649,835 A | | 3/1972 | Brackenbrough et al. |
| 4,143,273 A | | 3/1979 | Richey et al. |
| 4,489,426 A | | 12/1984 | Grass et al. |
| 4,766,603 A | | 8/1988 | Okabe et al. |
| 4,868,843 A | | 9/1989 | Nunan |
| 5,278,887 A | | 1/1994 | Chiu et al. |
| 5,342,301 A | | 8/1994 | Saab |
| 5,422,926 A | | 6/1995 | Smith et al. |
| 5,568,533 A | | 10/1996 | Kumazaki et al. |
| 5,621,779 A | | 4/1997 | Hughes et al. |
| 5,658,311 A | * | 8/1997 | Baden ........................... 606/192 |
| 6,168,610 B1 | * | 1/2001 | Marin et al. ................... 606/198 |
| 6,527,739 B1 | * | 3/2003 | Bigus et al. .............. 604/101.01 |
| 6,792,078 B2 | | 9/2004 | Kato et al. |
| 8,246,670 B2 | * | 8/2012 | Von Oepen et al. ......... 623/1.11 |
| 2005/0131446 A1 | * | 6/2005 | Coughlin et al. ............. 606/194 |
| 2006/0067481 A1 | | 3/2006 | Morton |
| 2007/0203562 A1 | * | 8/2007 | Malewicz et al. ............. 623/1.11 |
| 2009/0299374 A1 | * | 12/2009 | Tilson et al. ..................... 606/94 |

FOREIGN PATENT DOCUMENTS

JP    2005095345    4/2005

* cited by examiner

*Primary Examiner* — Melanie Tyson
(74) *Attorney, Agent, or Firm* — Oyen Wiggs Green & Mutala LLP

(57) ABSTRACT

Multi-balloon catheter structures that are able to move with respect to one another may provide superior compliance in tortuous passages to, for example, perform angioplasty and/or expand stents. Two or more balloons may be inflated to equal pressures. A length of the balloons may be sufficiently longer than a length of a stent to accommodate axial movement of the balloons. One or more balloons may be lubricous or carry a lubricant.

24 Claims, 23 Drawing Sheets

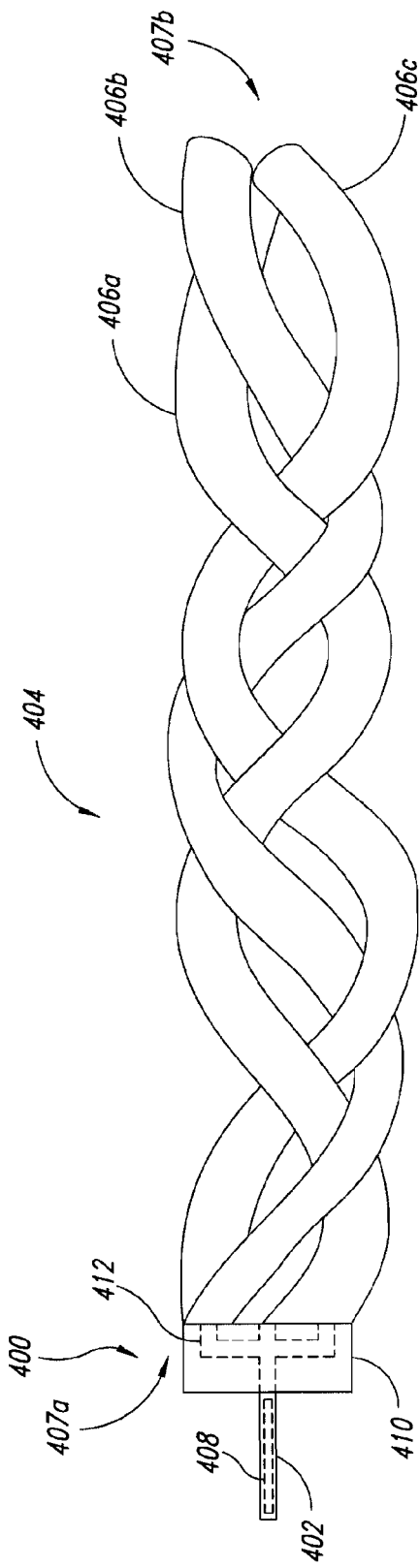
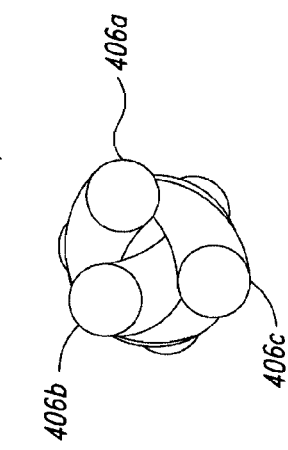
FIG. 4A
FIG. 4B

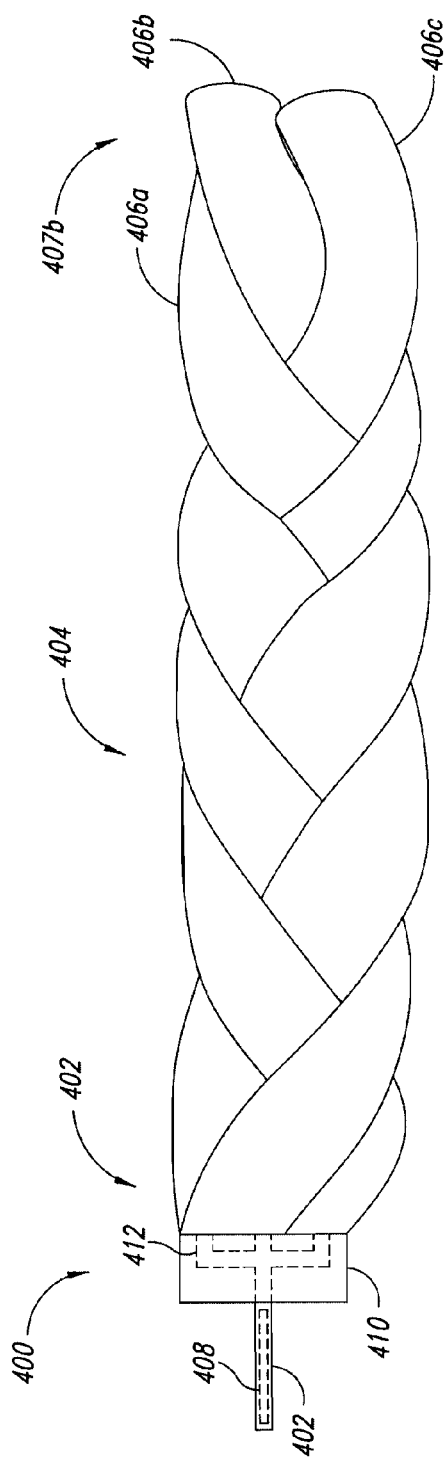
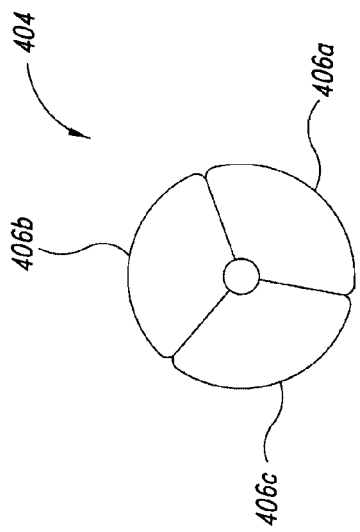
FIG. 4C
FIG. 4D

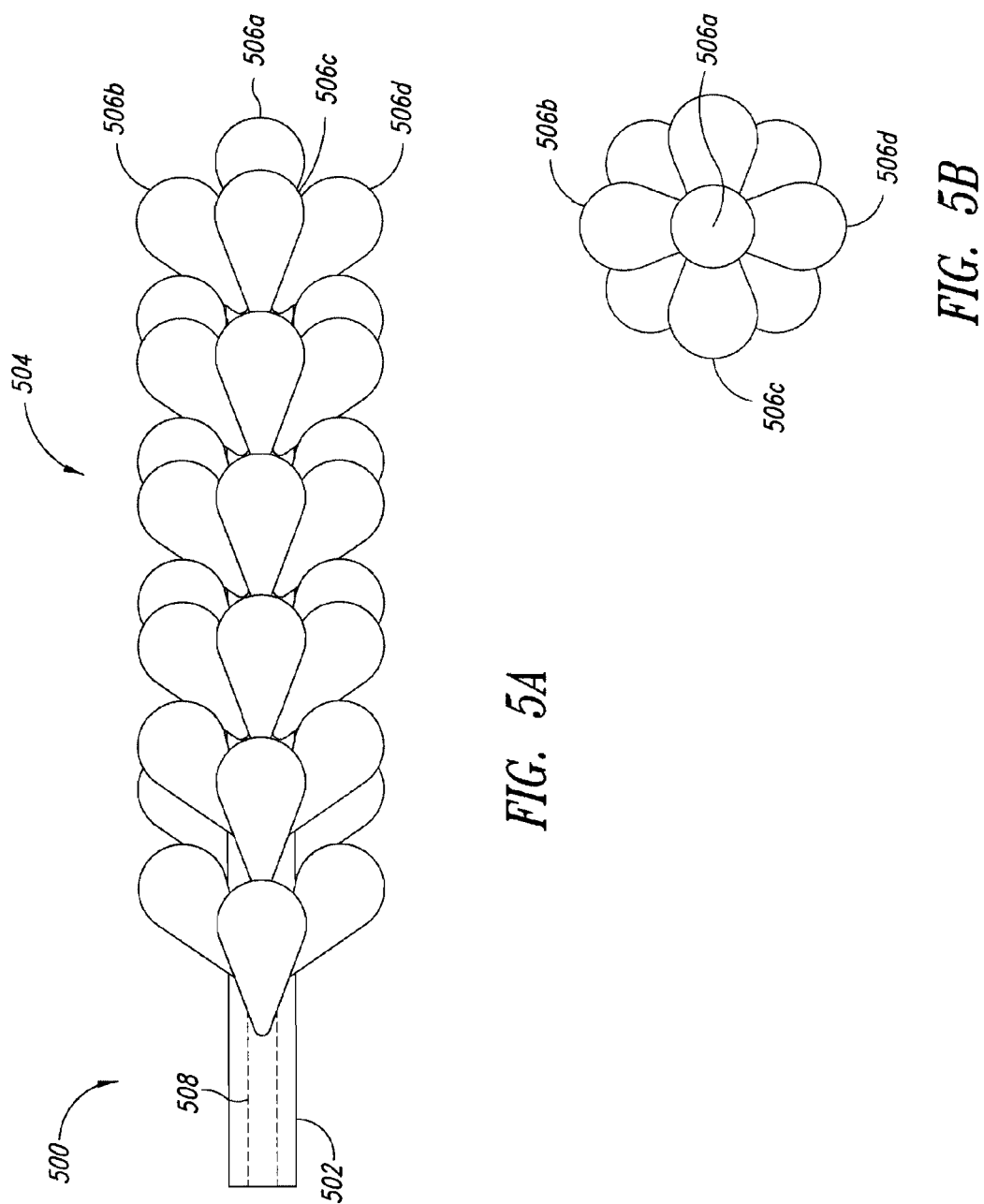

PROVIDE INFLATABLE STRUCTURE(S) HAVING A NECKED PORTION — 820

*FIG. 8B*

HEAT INFLATABLE STRUCTURE(S) IN CENTER PORTION — 822

*FIG. 8C*

ADHERE INFLATABLE STRUCTURE(S) IN CENTER PORTION — 824

*FIG. 8D*

FORM THROUGHHOLE — 826

*FIG. 8E*

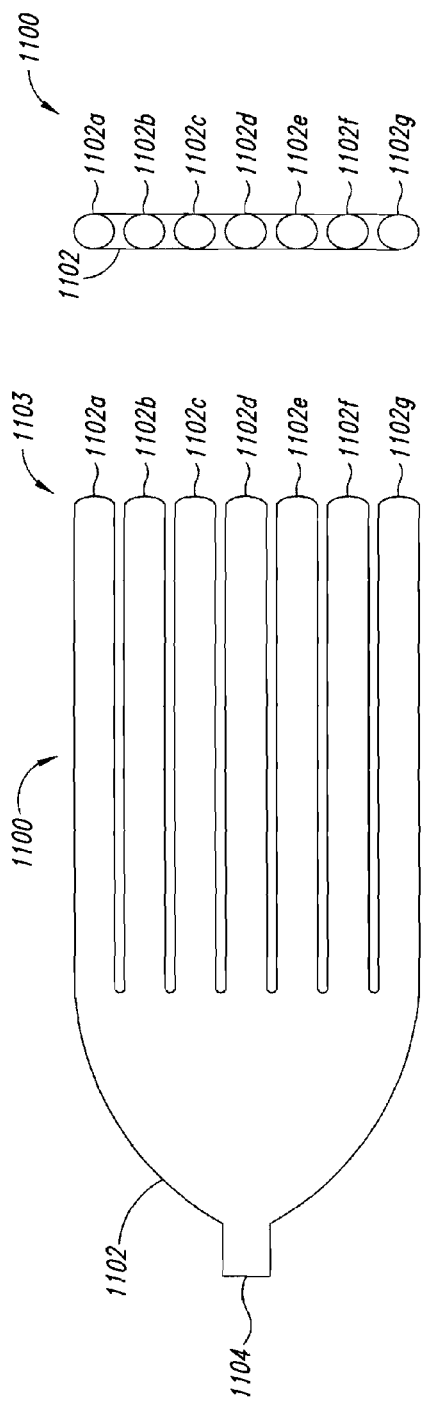
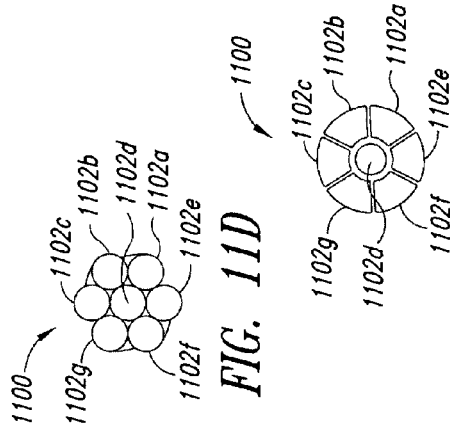
FIG. 11A  FIG. 11B  FIG. 11C  FIG. 11D  FIG. 11E

*FIG. 14B*
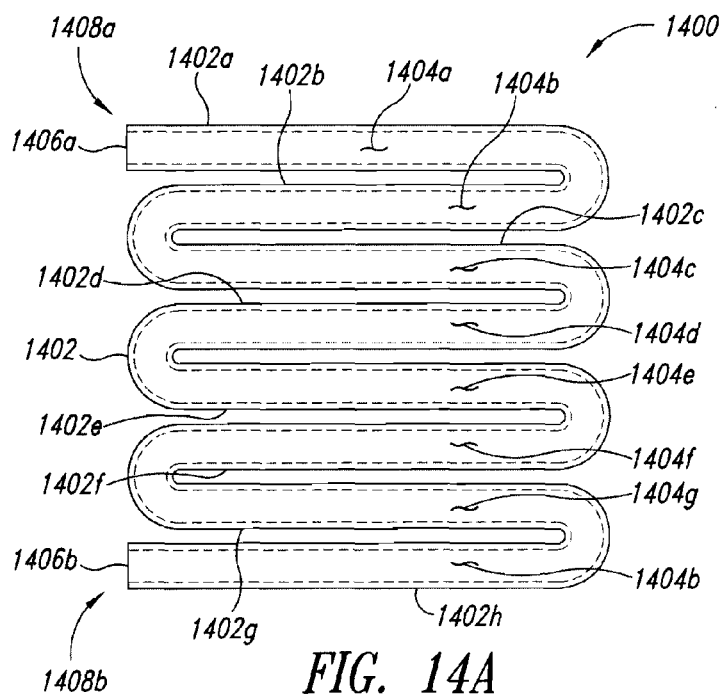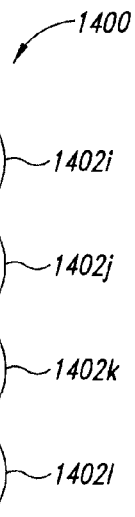
*FIG. 14A*  *FIG. 14C*
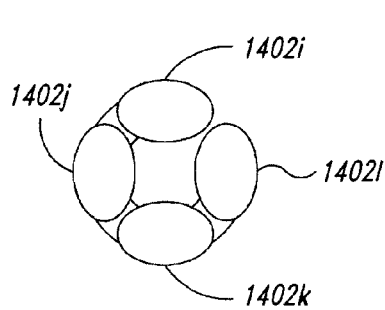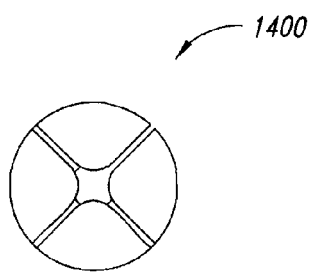
*FIG. 14D*  *FIG. 14E* form angioplasty and/or implant a stent over an appre-
IN VIVO INFLATABLE STRUCTURES, FOR EXAMPLE TO EXPAND STENTS

BACKGROUND

1. Technical Field

The present disclosure is related to in vivo medical devices, and more particularly to inflatable devices for use in bodily vessels or lumens, for example vasculature such as arteries.

2. Description of the Related Art

Numerous medical procedures now employ catheters to enter bodily vessels, for example vasculature such as arteries, veins, and or the heart. Such procedures are often percutaneous, providing numerous advantages over more traditional surgery, for example reduced trauma and faster healing. However, catheter procedures are often difficult to perform. Catheter procedures require a care provider (e.g., medical doctor or physician) to guide a catheter or guide wire through the vasculature to a desired position without direct visual feedback. The care provider may receive tactile feedback and/or secondary visual feedback. The secondary visual feedback may come from a camera mounted to the catheter or guide wire. The secondary visual feedback may alternatively come from detection of the catheter or guide wire using medical imaging systems for example ultrasound, computer tomography (CT), real-time magnetic resonance (MR), X-ray, fluoroscopy and/or other radiological apparatus and methods. In either case, the care provider does not have direct visual contact with the catheter or guide wire.

A variety of procedures referred to as angioplasty, widen vasculature and/or remove blockages from vasculature using an inflatable structure such as a balloon positioned at a distal end of a catheter. Often the procedure will include implantation of a structure such as a stent in vasculature to support the vasculature. While some stents are self-expanding, other stents are expanded to contact the wall of the vasculature using a balloon.

The catheter typically includes at least one inflation lumen which allows the balloon to be inflated and deflated and a guide wire lumen allowing the catheter to be guided in the bodily vessel. Balloons are typically made of flexible but inelastic materials, which do not appreciably stretch even when subjected to the high pressures (e.g., 10-30 ATM) commonly employed to inflate such balloons). Hence, the balloon is often folded when in an uninflated state or configuration to provide a relatively small cross sectional diameter. This allows the balloon to fit in the vasculature and/or to fit in the catheter. Rather than stretching, the balloon unfolds in response to inflation, to provide a relatively large cross sectional diameter when in an inflated state or configuration. This allows the balloon to physically engage the walls of the vasculature and/or expand the stent to physically engage the walls of the vasculature.

Typically, catheters must travel a tortuous path through the vasculature. Flexible catheters and/or guide wires have been developed to facilitate such travel. Flexible stents are also now available, which facilitate travel through the vasculature. However, the flexibility of such stents tends to be limited by the flexibility of the inflation balloon. Consequently, numerous short stents may be employed to provide support to an appreciable length of the vasculature. Each stent requires a respective balloon which increases the complexity of the catheter procedure, which as previously noted is a difficult procedure to perform. Using multiple short stents also leads to discontinuities of vasculature.

Improvements in devices and methods associated with catheter based medical procedures are highly desirable.

BRIEF SUMMARY

Applicants have recognized that it may be advantageous to perform angioplasty and/or implant a stent over an appreciable length of vasculature. Applicants have also recognized that existing balloons are too rigid to easily travel the tortuous path of some lumens, for example some vasculature. Applicants have further recognized that existing balloons apply a high straightening force when used over an appreciable length of a lumen such as vasculature, therefore significantly deforming the vasculature, resulting in sharp or unnatural configurations or discontinuities (e.g., unsmooth changes in direction) of the vasculature. At least some scientific literature suggests that sharp or abrupt angles in vasculature may lead to medical problems, for example increasing the risk of further blockages. Applicants have additionally recognized that existing balloons, when inflated, are too rigid to apply a uniform force over an entire length of a flexible stent or over multiple stents, particularly when the position of the stent or stents is in a tortuous section of the lumens such as vasculature. Balloons made of elastic material, in attempt to overcome the rigidity in inflated states, are unstable as they tend to inflate excessively in less restrictive areas and not keep the desired tubular shape. Maintaining of a tubular shape with high force and high uniformity of radial expansion, but with low bending stiffness is highly desirable. In conventional inflated balloon, such properties are contradictory. For example, when a balloon is made of inelastic material, the bending force is too high when the balloon is inflated. However if a balloon is made of very elastic material, radial expansion is irregular and not self limiting. When a balloon is made in the shape of a bellows, the bellows shape is imparted to the expanded stent, which is undesirable. Applicants have further recognized that it may be advantageous to employ such balloons in a variety of bodily lumens other than vasculature, including but not limited to: airways, bronchi, trachea; gastro-intestinal such as the esophagus, stomach, intestines for instance the small intestine and/or colon (e.g., ascending, transverse, descending, sigmoid) and rectum; hepatobiliary structures (e.g., common bile duct, inter-hepatic ducts); genitourinary (ureters, urethral, prostatic, fallopian tubes, uterine); sinuses (frontal, ethmoid) and/or lymphatic structure.

At least one embodiment may be summarized as an in vivo article, including a first inflatable structure having a port and at least one distal-most portion spaced most distally from the port of the first inflatable structure; and at least a second inflatable structure having a port and at least one distal-most portion spaced most distally from the port of the second inflatable structure, the second inflatable structure physically coupled to the first inflatable structure for intravascular travel therewith, the at least one distal-most portions of each of at least the first and the second inflatable structures moveable with respect to one another in response to inflation of at least one of the first and the second inflatable structures from a relatively less inflated state to a relatively more inflated state, the first and the second inflatable structures sized to be received in a lumen of a body.

The inflatable structures may take the form of elongated balloons. The distal-most portions of the inflatable structures may be axially movable with respect to one another in response to inflation of at least one of the first and the second inflatable structures from the relatively less inflated state to the relatively more inflated state. The balloons may extend generally parallel to one another along over at least half a length of the balloons. The elongated balloons may be helically disposed about respective axes that extend generally parallel to one another along over at least half a length of the balloons. The elongated balloons, may each have at least two arms that extend generally parallel to one another along over at least half a length of the balloons. Ports of the inflatable structures may be fluidly communicatively coupled to one another. The balloons may be made of flexible but inelastic material, which are folded in the relatively less inflated state and at least partially unfolded in the relatively more inflated state. The in vivo article may further include a catheter having at least one lumen, the catheter physically coupled to the inflatable structure to move the inflatable structures through vasculature and the at least one lumen fluidly coupled to an interior of at least one of the inflatable structures. The in vivo article may further include at least a third inflatable structure having a port and at least one distal-most portion spaced most distally from the port, the third inflatable structure physically coupled to the first inflatable structure for in vivo travel therewith, the at least one distal-most portions of each of at least the third inflatable structure axially moveable with respect to the distal-most portions of the first and the second inflatable structures in response to inflation of at least one of the first and the second inflatable structures from a relatively less inflated state to a relatively more inflated state.

At least one embodiment may be summarized as an catheter device including a first inflatable balloon; a second inflatable balloon; at least a third inflatable balloon; and a catheter having at least one lumen, the catheter physically coupled to move at least the first, the second and the third inflatable balloons through vasculature and the at least one lumen fluidly coupled to an interior of at least one of the first, the second, and the third inflatable balloons.

Each of the inflatable balloons may respectively have a distal-most end portion, the distal-most portions axially slideable with respect to one another during at least an initial portion of inflation of the inflatable balloons. The inflatable balloons may each have at least two arms and a port positioned between the two arms, a terminus of each of the arms being the distal-most end portions of the first, the second and at least the third inflatable balloons. At least one of the inflatable balloons may have a narrowed portion extending between the two arms. Ports of the inflatable balloons may be commonly fluidly communicatively coupled. The in vivo catheter device may further include a nipple extending from at least one of the ports.

At least one embodiment may be summarized as a medical article including a first inflatable balloon; and at least a second inflatable balloon coupled to at least partially axially overlap the first inflatable balloon, wherein an internal pressure of the second inflatable balloon is equal to an internal pressure of the first inflatable balloon when inflated during use. The inflatable balloons may each have a respective port, the ports commonly fluidly coupled. The medical article may further include a manifold that equally distributes fluid to each of at least the first and the second inflatable balloons during inflation.

At least one embodiment may be summarized as a catheter device to expand a stent, the catheter device including a catheter having at least one lumen; and at least a first inflatable balloon having a length sufficiently longer than a length of the stent such that the first inflatable balloon physically interacts over an entire length of the stent when the first inflatable balloon is inflated and bent, the first inflatable balloon physically coupled to the catheter to move through vasculature therewith, an interior of at least the first inflatable balloon fluidly coupled with the at least one lumen of the catheter.

The inflatable balloons may be longer than the length of the stent by an amount greater than a product of pi times a change in a radial dimension of the first inflatable balloon between an un-inflated state and a maximally inflated state. The inflatable balloons may be longer than the length of the stent by an amount greater than a sum of a contraction length and a product of pi times a change in a radial dimension of the first inflatable balloon between an un-inflated state and a maximally inflated state.

At least one embodiment may be summarized as a medical article including a plurality of inflatable balloons sized to be received in a bodily lumen, for example intravascularly, in at least partially overlapping relation; and a lubricant carried by at least one of the inflatable balloons to lower a friction coefficient between the inflatable balloons in at least a partially inflated state.

The inflatable balloons may include at least one central balloon that carries the lubricant and at least two outer balloons that are each physically in contact with the central balloon and which do not carry the lubricant. Each of the balloons in the plurality of balloons may carry the lubricant.

At least one embodiment may be summarized as a method of forming an in vivo inflation device, including providing a first inflatable structure, the first inflatable structure being elongated and having a pair of opposed ends; providing a second inflatable structure, the second inflatable structure being elongated and having a pair of opposed ends; physically coupling the first and the second inflatable structures to one another between the pair of opposed ends; and forming a port that provides fluid access into a respective interior of each of the first and the second inflatable structures.

The method may further include providing a third inflatable structure, the third inflatable structure being elongated and having a pair of opposed ends; physically coupling the third inflatable structure to at least one of the first and the second inflatable structures between the respective pairs of opposed ends. Forming a port that provides fluid access into a respective interior of each of the first and the second inflatable structures may include forming the port to also provide fluid access into a respective interior of the third inflatable structure. Providing a first inflatable structure may include providing a first inflatable structure having a necked portion between the pair of opposed ends. Physically coupling the first and the second inflatable structures may include heating at least one of the first and the second inflatable structures in a center portion located between the pair of opposed ends. Physically coupling the first and the second inflatable structures may include adhering at least one of the first and the second inflatable structures in a center portion located between the pair of opposed ends. Forming a port may include forming a throughhole through at least a portion of the first and the second inflatable structures. The method my further include providing a nipple extending from the port. The method may further include providing a lubricant on at least a portion of an exterior of at least one of the first and the second inflatable structures.

At least one embodiment may be summarized as an in vivo medical article including a first structure having a port and a number of inflatable chambers formed therein, at least two of the inflatable chambers having distal-most portions spaced most distally from the port, at least a portion of the at least two inflatable chambers moveable with respect to one another in response to inflation of at least one of the first and the second inflatable chambers from a relatively less inflated state to a relatively more inflated state, the first structure sized for in vivo travel in the relatively less inflated state.

The distal-most portions of the inflatable chambers may be axially movable with respect to one another in response to inflation of at least one of the inflatable chambers from the relatively less inflated state to the relatively more inflated state. The first structure may include at least three inflatable chambers. The inflatable chambers may be slideable with respect to one another in response to inflation of at least one of the inflatable chambers from the relatively less inflated state to the relatively more inflated state. The first structure may take the form of a balloon and the inflatable chambers may take the form of elongated portions of the balloon that extend generally parallel to one another along over at least half a length of the balloon when in the relatively more inflated state. The first structure may be a balloon and the inflatable chambers may be elongated portions of the balloon that extend between a number of narrowed portions of the balloon. The balloon may have a number of folds that each form a respective one of the narrowed portions between the inflatable chambers. The first structure may be a balloon and the inflatable chambers may be elongated portions of the balloon that are fluidly communicatively coupled in series. The first structure may have a second port fluidly communicatively coupled to the first port by the inflatable chambers. The first structure may take the form of a balloon and the inflatable chambers may take the form of elongated fingers of the balloon that are fluidly communicatively coupled in parallel. The balloon may be an inelastic balloon, which is folded in the relatively less inflated state and at least partially unfolded in the relatively more inflated state. The in vivo article may further include a catheter having at least one lumen, the catheter physically coupled to the first structure to move the first structure through vasculature and the at least one lumen fluidly coupled to at least one of the inflatable chambers of the first structure. An internal pressure of a first one of the inflatable chambers may be equal to an internal pressure of a second one of the inflatable chambers when inflated during use. The first structure may take the form of a balloon and the inflatable chambers may take the form of elongated portions of the balloon, the elongated portions having a length sufficiently longer than a length of a stent to be expanded by the balloon such that the elongated portions physically interacts over an entire length of the stent when the balloon is inflated while bent. The elongated portions of the balloon may be longer than the length of the stent by an amount greater than a product of pi times a change in a radial dimension of the inflatable portions between an un-inflated state and a maximally inflated state. The first inflatable balloon may be longer than the length of the stent by an amount greater than a sum of a contraction length and a product of pi times a change in a radial dimension of the first inflatable balloon between an un-inflated state and a maximally inflated state. The in vivo article may further include a lubricant carried by at least one of the elongated portions of the balloon to lower a friction coefficient between the elongated portions of the balloon in at least a partially inflated state. The elongated portions may have at least one central portion that carries the lubricant and at least two outer portions that are each physically in contact with the central portion and which do not carry the lubricant. Each of the elongated portions of the balloon may carry the lubricant.

At least one embodiment may be summarized as a method of forming an in vivo inflation device including providing a first structure, the first structure having at least two elongated fingers; providing a second structure, the second structure having at least two elongated fingers; physically coupling the first and the second structures to one another to form a first chamber and at least a second chamber in respective ones of the elongated fingers; and providing a port that provides fluid access into the first and at least the second chambers.

The method may include forming at least a third elongated finger.

Physically coupling the first and the second structures may include heating at least a portion of at least one of the first and the second structures about a periphery thereof. Physically coupling the first and the second structures may include adhering at least a portion of at least one of the first and the second inflatable structures about a periphery thereof. The method may further include providing a manifold having a fluid passage in fluid communication with the first and at least the second chambers. The method may further include providing a lubricant on at least a portion of an exterior of at least one of the first and the second inflatable structures. The method may further include folding at least one of the first and the second inflatable structures.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 4A is a side elevational view of a catheter device including a flexible elongated member, a manifold, and an expansion structure formed by a plurality of inflatable structures helically wound with respect to one another, according to one illustrated embodiment.

FIG. 4B is a front elevational view of the device of FIG. 4A, showing the inflatable structures in an uninflated state or configuration, according to one illustrated embodiment.

FIG. 4C is a side elevational view of the device of FIG. 4A showing the inflatable structures in an inflated state or configuration, according to one illustrated embodiment.

FIG. 4D is a front elevational of the device of FIG. 4A, showing the inflatable structures in an inflated state or configuration.

FIG. 5A is a side elevational view of a catheter device including a flexible elongated member and an expansion structure formed by a plurality of inflatable structures, according to another illustrated embodiment, showing the inflatable structures in an inflated state or configuration.

FIG. 5B is a front elevational view of the catheter device of FIG. 5A.

FIG. 8B is a flow diagram showing a method of providing inflatable structures having neck portions, according to one illustrated embodiment.

FIG. 8C is a flow diagram showing a method of physically securing the inflatable structures to one another, according to one illustrated embodiment.

FIG. 8D is a flow diagram showing a method of physically securing the inflatable structures to one another, according to another illustrated embodiment.

FIG. 8E is a flow diagram showing a method of forming a port in an inflatable according to another illustrated embodiment.

FIG. 11A is a side elevational view of an expansion structure formed from an inflatable balloon including a plurality of inflatable chambers, according to one illustrated embodiment.

FIG. 11B is a front elevational view of the expansion structure of FIG. 11A.

FIG. 11C is an isometric view of the expansion structure of FIG. 11A.

FIG. 11D is a front elevational view of the expansion structure of FIG. 11A in an uninflated state or configuration, where a structure that forms a number of outer ones of the chambers is wrapped around a structure that forms an inner one of the chambers, according to one illustrated embodiment.

FIG. 11E is a front elevational view of the expansion structure of FIG. 11D, in an inflated state or configuration.

FIG. 14A is a top plan view of an expansion structure having multiple inflatable chambers in an unfolded configuration, according to another illustrated embodiment.

FIG. 14B is a side elevational view of the expansion structure of FIG. 14A.

FIG. 14C is a front view of the expansion structure of FIG. 14A in an uninflated state or configuration, where a structure that forms a number of outer ones of the chambers is wrapped around a structure that forms an inner one of the chambers, according to one illustrated embodiment.

FIG. 14D is a front view of the expansion structure of FIG. 14A in an uninflated state or configuration, where a structure that forms a number of outer ones of the chambers is wrapped around a structure that forms an inner one of the chambers, according to one illustrated embodiment.

FIG. 14E is a front view of the expansion structure of FIG. 14A in an inflated state or configuration, where a structure that forms a number of outer ones of the chambers is wrapped around a structure that forms an inner one of the chambers, according to one illustrated embodiment.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with stents, catheters, balloons, fluid delivery subsystems and/or image based or other location determination subsystems have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
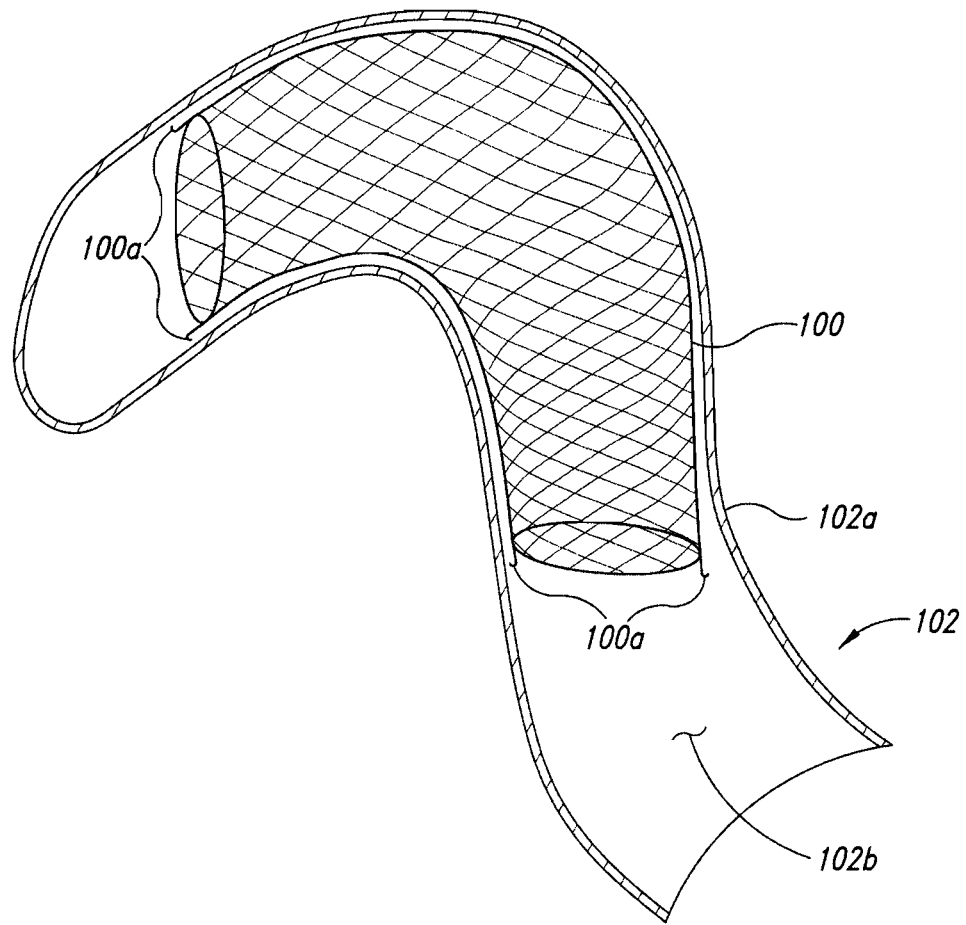
FIG. 1 is a cross sectional view of a bodily vessel with a flexible stent deployed therein according to one illustrated embodiment.

FIG. 1 shows a flexible stent 100 in a portion of a bodily vessel 102 according to one illustrated embodiment.

The bodily vessel 102 may take a variety of forms, for example an artery, vein, or other vasculature; airways, bronchi, trachea; gastro-intestinal tract such as the esophagus, stomach, intestines for instance the small intestine and/or colon (e.g., ascending, transverse, descending, sigmoid) and rectum; hepatobiliary structures (e.g., common bile duct, inter-hepatic ducts); genitourinary system (ureters, urethral, prostatic, fallopian tubes, uterine); sinuses (frontal, ethmoid) and/or lymphatic structure. A wall 102a of the vessel 102 defines at least one passage or lumen 102b. The lumen 102a of the bodily vessel 102 may present a torturous path through which the stent 100 must travel to reach a desired position.

The stent 100 may take a variety of forms, for example a balloon expandable stent. The balloon expandable stents 100 may have various forms, for example tube, wire, sheet or ribbon stents. Balloon expandable stents 100 may be formed of a variety of materials, for example stainless steel, tantalum, nitinol, platinum iridium, polymers, niobium alloy, or cobalt alloys. Balloon expandable stents 100 may be formed by way of a variety of processes, for example laser cutting, photochemical etching, electronic discharge machining, water jet cutting, braiding or knitting. Balloon expandable stents may also have a variety of geometries, for example coil, helical spiral, woven, individual rings unconnected, open cell, closed cell, peak-to-peak, peak-to-valley and hybrids. Helical spirals geometries may, for example, be integral, have an axial spine, have no or minimal connections of periodic peak-to-peak connections. Woven geometries may, for example, be braided or knitted. Closed cell geometries may, for example, include regular peak-to-peak connections, with non-flexible connectors, flexible connectors or a combination of flexible and non-flexible connectors.

The stent 100 may include one or more structures such as hooks] that anchor, implant or otherwise secure the stent 100 to the wall 102a of the bodily vessel 102 at a desired position. The stent 100 may travel through the lumen 102b in a compressed or non-expanded configuration, for example being advanced via a catheter. The stent 100 may be expanded to physically engage the wall 102a at the desired position, for example using an expansion structure formed from two or more inflatable structures. As discussed in more detail below, the inflatable structures may take the form of one or more balloons with one or more inflatable chambers.

Figure 2:
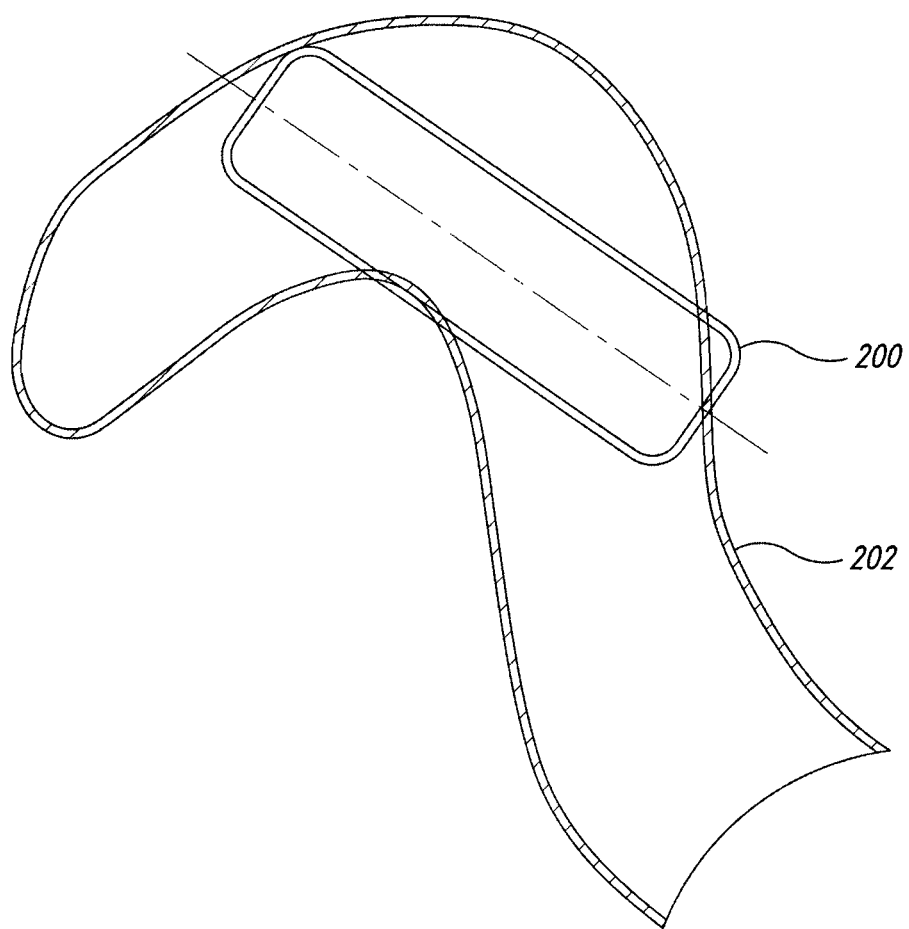
FIG. 2 is a cross sectional view of the bodily vessel of FIG. 1, showing a relative position of a rigid inflated balloon with respect to the bodily vessel.

FIG. 2 shows a profile of a conventional inflatable structure such as a balloon 200, illustrated overlying a bodily vessel 202. Conventional balloons are rigid when inflated, resulting in a stiff rigid structure relative to the vessel 202. Thus, inflation of the balloon 200 may likely cause the balloon 200 to deform the bodily vessel 202 into an unnatural configuration with discontinuities. At least some scientific literature suggests that sharp or abrupt angles or discontinuities in vasculature may lead to medical problems, for example increasing the risk of blockages.

Figures 3A, 3B:
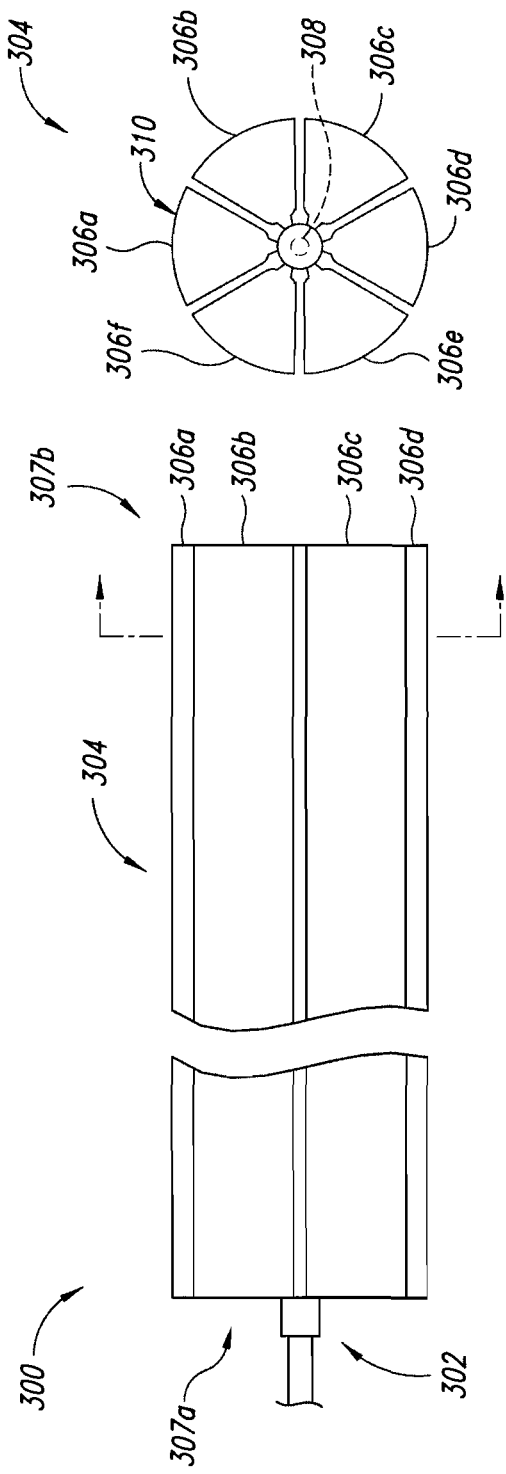
FIG. 3A is a side elevational view of a catheter device including an elongated flexible member and an expansion structure formed by a plurality of elongated inflatable structures, according to one illustrated embodiment.
FIG. 3B is a front elevational view of the catheter device of FIG. 3A, showing the inflatable structures in an inflated state or configuration.

FIG. 3A shows a catheter device 300, according to one illustrated embodiment.

Figure 19:
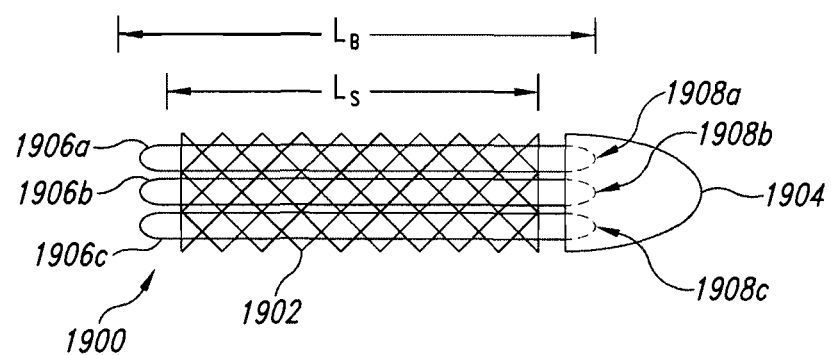
FIG. 19 is a schematic diagram showing a change in lateral movement in a torturous path.

The catheter device 300 includes a flexible elongated member 302 and an expansion structure 304 positioned at least proximate one end of the flexible elongated member 302. The expansion structure 304 includes a plurality of inflatable structures such as balloons 306a-306f (collectively 306). The balloons 306 may extend generally parallel to one another. A first end 307a of the balloons may be secured with respect to one another, while a second end 307b of the balloons 306 are able to move with respect to one another. In particular, the second ends 307b may move axially with respect to one another. In at least some embodiments where the balloons 306 are to be used with stents, the balloons 306 should have a length that is longer than a length of the stent, by an amount sufficient to accommodate axial movement between the balloons when in a tortuous portion of a bodily vessel. Such is discussed in more detail with reference to FIG. 19, herein.

The balloons 306 individually have a smaller cross sectional area than a single balloon would have that could expand to have at least approximately the same cross sectional diameter as the plurality of balloons would have collectively. The balloons 306 may also have a smaller wall thickness than a single balloon capable of the expanding to the same cross sectional diameter. Thus, the expansion structure 304 employing a plurality of balloons 306 is more flexible than a single balloon expansion structure of similar size. Allowing the balloons 306 to move, for example axially, with respect to one another helps to ensure that the expansion structure 304 maintains the maximum flexibility provide by the use of the plurality of balloons with smaller cross sectional areas than a single balloon structure. Such allows the balloons 306 to be compliant, as the balloons inflate. The compliance of the balloons 306 may, for example, decrease as they inflate, but may remain sufficiently compliant to the point of maximum inflation, at which point the balloons 306 will have the desired shape. Increasing friction as the balloons 306 reach maximum inflation may make it desirable to form one or more of the balloons 306 from an inherently lubricious material. Applying a dry or wet lubricant to an exterior of one or more of the balloons 306 may assist in maintaining the maximum flexibility of the expansion structure 304. Such flexibility may facilitate travel of the expansion structure 304 over tortuous vasculature paths. Such flexibility may also allow the expansion structure 304 to apply force over a longer length of the vasculature than a single balloon structure without creating significant bends, edges, unnatural shapes or discontinuities in the vasculature. Such flexibility may also allow the expansion structure 304 to apply a uniform force over an entire length of a flexible stent. Such flexibility may allow the use of longer flexible stents, and possibly eliminate the need to use several shorter stents. Such flexibility may allow the implantation of stents in particular tortuous portions of the vasculature.

The balloons 306 include interiors or chambers which may be fluidly communicatively coupled to one or more lumens 308 of the flexible elongated member 302. As illustrated in FIG. 3B, the balloons 306 may be inflated from a relatively uninflated state or configuration into a relatively inflated state or configuration by providing fluid to the interior of the balloons via the lumen 308.

In some embodiments, the balloons 306 are made of inelastic material and hence do not appreciably stretch when unfolding even under relatively high pressures associated with balloons that expand stents. Thus, one or more of the balloons 306 may be in a folded configuration, such as that illustrated in FIG. 3C, which provides a cross section having a relatively small or reduced diameter for travel through the bodily vessel to the desired position. In response to inflation, the balloon 306 unfolds (as illustrated by arrows) into the relatively inflated state or configuration, for example as illustrated by broken lines in FIG. 3C. In some embodiments, the balloons 306 may be elastic, appreciably stretching when inflated. In such embodiments the balloons 306 may or may not be folded since the profile or cross-section of the balloons 306 will be relatively small when uninflated versus when inflated. The balloons 306 may also be deflated, allowing removal of the balloons 306, for example after the balloons 306 have expanded a stent.

Individual balloons 306 when expanded or unfolded may have a generally circular undeformed cross section. Such balloons are advantageously easy and inexpensive to manufacture as compared to more complex geometries. Where two or more of the balloons 306 are grouped together, neighboring balloons 306 may physically interfere with one another as the balloons 306 inflate and unfold. (The adjacent portions of the balloons 306 are shown with a space therebetween in order to illustrate the individual balloons. In actual use, the adjacent portions of the balloons 306 would be physically touching one another, physical interfering with expansion. A similar convention is applied in the other Figures that illustrate inflated balloons.) Thus, the balloons 306 which might otherwise have a circular cross section may have a wedge or pie shape cross section, best illustrated in FIG. 3B. Notably, an outer perimeter portion 310 (only one called out in FIG. 3B) of each of the balloons 306 is approximately arcuate, and the group of balloons 306 have a substantially circular cross section.

Figure 3C:
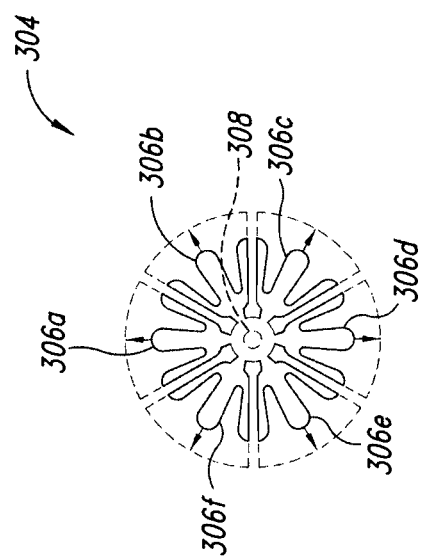
FIG. 3C shows a front elevational view of the inflatable structures of FIG. 3A, showing the inflatable structures in an uninflated state or configuration, according to one illustrated embodiment.
Figure 3D:
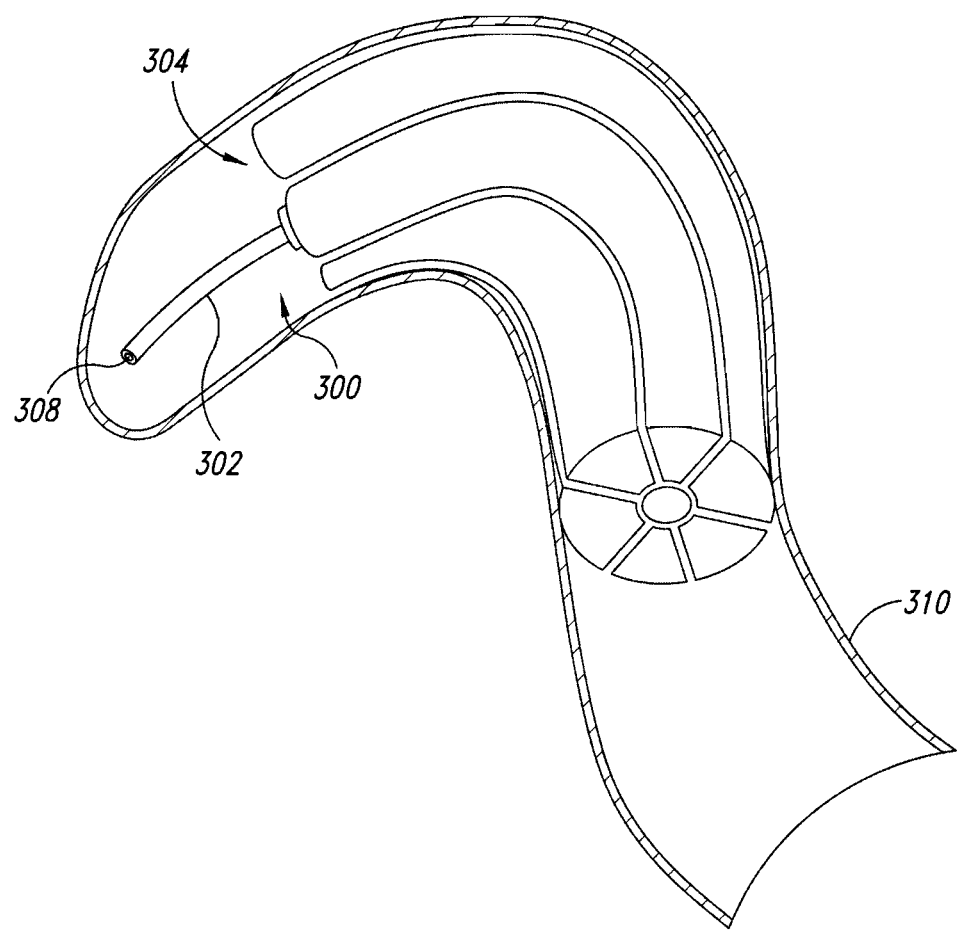
FIG. 3D is a cross sectional view of a bodily vessel with the catheter device of FIG. 3A positioned therein, according to one illustrated embodiment.

FIG. 3D shows the expansion structure 304 at a desired position (e.g., implant position) in a bodily vessel 310. The expansion structure 304 may be advanced through the bodily vessel 310 using the flexible elongated member 302 of the catheter device 300. When in the desired position, fluid can be provided via one or more lumens 308 of the flexible elongated member 302 to inflate the balloons 306, causing the balloons to unfold into the relatively inflated state or configuration. Thus the balloons 306 move from a relatively less inflated state or configuration, illustrated in FIG. 3C, to a relatively more inflated state configuration, illustrated in FIG. 3B.

FIGS. 4A and 4B show a catheter device 400, according to another illustrated embodiment.

The catheter device 400 includes a flexible elongated member 402 and an expansion structure 404 positioned at least proximate one end of the flexible elongated member 402. The expansion structure 404 includes a plurality of inflatable structures such as balloons 406a-406c (collectively 406). The balloons 406 may be helically wound or positioned with respect to one another. A first end 407a of the balloons are secured with respect to one another, while a second end 407b of the balloons are able to move with respect to one another. In particular, the ends 407b may move axially with respect to one another. As previously noted, where the balloons 406 are to be used with stents, the balloons 406 should have a length that is longer than a length of the stent, by an amount sufficient to accommodate axial movement between the balloons 406 when in a tortuous portion of a bodily vessel. As previously noted, the use of a plurality of balloons 406 individually having a smaller cross sectional area than a single balloon, which may move with respect to one another and/or which may be lubricous or carry a lubricant allows the expansion structure 404 to be more flexible than a single balloon expansion structure of similar size, providing numerous possible advantages.

The balloons 406 include interiors or chambers which may be fluidly communicatively coupled to one or more lumens 408 of the flexible elongated member 402 by one or more manifolds 410. Passages 412 in the manifold 410 are illustrated in broken line. The balloons 406 in FIGS. 4A and 4B are illustrated in a relatively uninflated state or configuration. As noted previously, the balloons 406 may be inelastic and do not appreciable stretch even under relatively high pressures associated with balloons that expand stents. Thus, one or more of the balloons 406 may in a folded configuration in the relatively uninflated state or configuration to reduce an overall diameter of a cross section of the expansion structure 404 for travel through the bodily vessel. In some embodiments, the balloons 406 are elastic, appreciably stretching when inflated. In such embodiments the balloons 406 may or may not be folded since the profile or cross-section of the balloons 406 will be relatively small when uninflated versus when inflated. The balloons 406 may also be deflated, allowing removal of the balloons 406, for example after the balloons 406 have expanded a stent.

FIGS. 4C and 4D show the catheter device 400 in a relatively more inflated state or configuration. The balloons 406 may unfold in response to inflation. In some embodiments, individual balloons 406 may have a generally circular undeformed cross section. Where two or more of the balloons 306 are grouped together, neighboring balloons 406 may physically interfere with one another as the balloons 406 inflate and unfold. Thus, the balloons 406 which might otherwise have a circular cross section may have a wedge or pie shape cross section, best illustrated in FIG. 4D. Notably, an outer perimeter portion of each of the balloons 406 is approximately arcuate, and the group of balloons 406 have a substantially circular cross section.

FIGS. 5A and 5B show a catheter device 500 according to another illustrated embodiment.

The catheter device 500 includes a flexible elongated member 502 and an expansion structure 504. The expansion structure 504 may include a plurality of inflatable structures, for example balloons 506a-506c (collectively 506, only three called out in the Figures). The balloons 506 may extend out radially and forwardly from the flexible elongated member 502. The balloons 506 may be distributed about a periphery of the flexible elongated member 502 to extend out at various angles. For example, balloons 506 may extend at angles of 90° distributed about the periphery. Alternatively, balloons 506 may extend at angles of 4520 distributed about the periphery. Alternatively, balloons 506 may extend at angles of 30° distributed about the periphery. Alternatively, balloons 506 may extend at angles of 15° distributed about the periphery. Other angles may also be suitable. One end of each balloon 506 is fixed to the flexible elongated member 502, while the other end of the balloons 506 are free to move relative to one another. As previously noted, where the balloons 506 are to be used with stents, the balloons 506 should have a length that is longer than a length of the stent, by an amount sufficient to accommodate axial movement between the balloons 506 when in a tortuous portion of a bodily vessel. As previously noted, the use of a plurality of balloons 506 individually having a smaller cross sectional area than a single balloon, which may move with respect to one another and/or which may be lubricous or carry a lubricant allows the expansion structure 504 to be more flexible than a single balloon expansion structure of similar size, providing numerous possible advantages.

The balloons 506 include interiors or chambers which may be fluidly communicatively coupled to one or more lumens 508 of the flexible elongated member 502. The balloons 506 may be inflated from a relatively uninflated state or configuration into a relatively inflated state or configuration by providing fluid to the interior of the balloons via the lumen 508.

As previously noted, in some embodiments the balloons 506 are inelastic and hence do not appreciably stretch even under relatively high pressures associated with balloons that expand stents. Thus, one or more of the balloons 506 may be in a folded configuration, which provides a cross section having a relatively small or reduced diameter for travel through the bodily vessel to the desired position. In response to inflation, the balloon 506 unfolds into the relatively inflated state or configuration. In some embodiments, the balloons 506 are elastic, appreciably stretching when inflated. In such embodiments the balloons 506 may or may not be folded since the profile or cross-section of the balloons 506 will be relatively small when uninflated versus when inflated. The balloons 506 may also be deflated, allowing removal of the balloons 506, for example after the balloons 506 have expanded a stent.

Figure 6A:
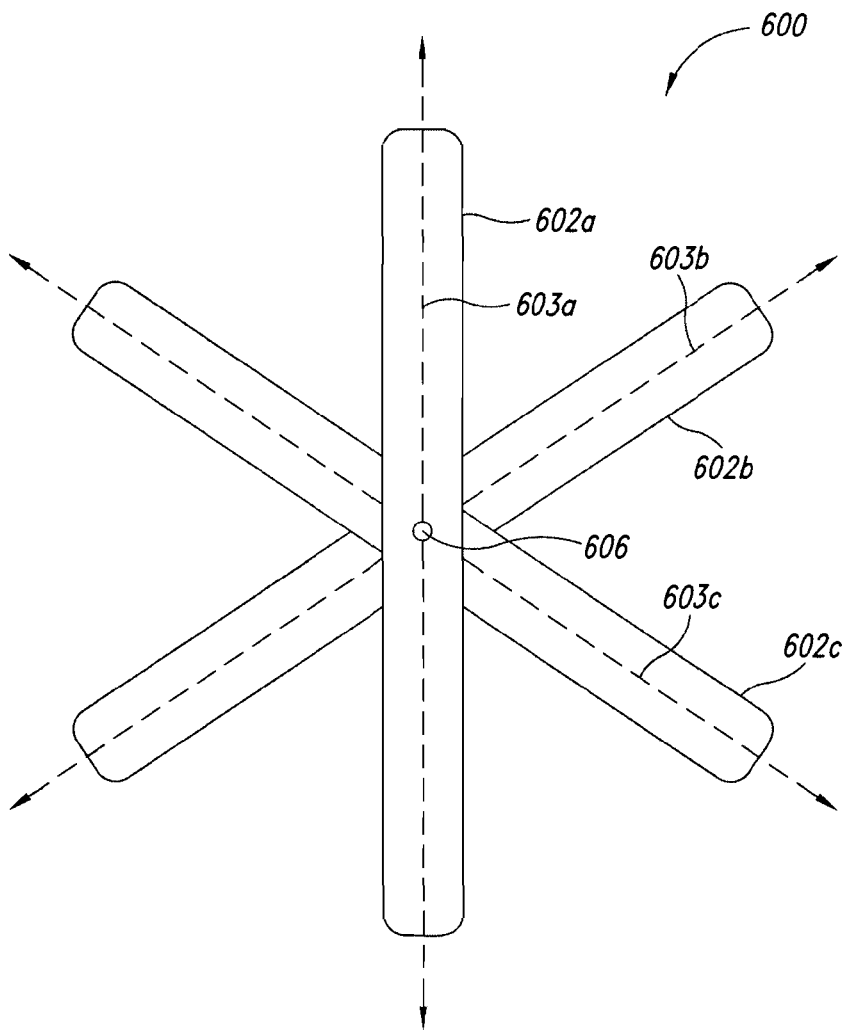
FIG. 6A is a top plan view of three balloons overlying one another to form a multi-balloon expansion structure, according to one illustrated embodiment.
Figure 6B:
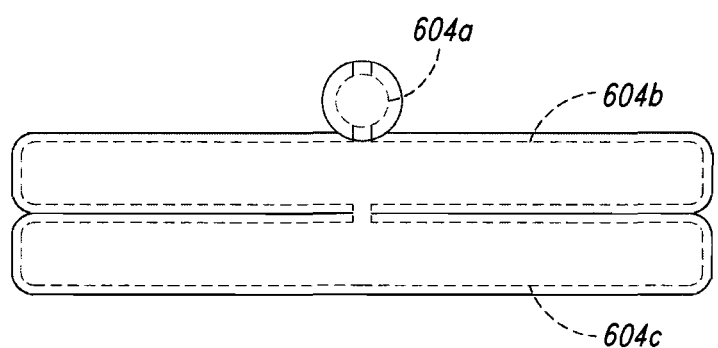
FIG. 6B is a side elevational view of the multi-balloon expansion structure of FIG. 6A.

FIGS. 6A and 6B show an expansion structure 600, according to one illustrated embodiment.

The expansion structure 600 is formed from a number of inflatable structures such as balloons 602a-602c (collectively 602). The balloons 602 are elongated and each balloon 602 has a respective longitudinal axis 603a-603c (collectively 603). The balloons 602 are laid out with the longitudinal axes 603 oriented at angles with respect to one another.

As best illustrated in FIG. 6B, the balloons 602 may be stacked one on top of the other, and each balloon 602 includes one or more respective chambers, shown in broken line in FIG. 6B as 604a-604c (collectively 604). As will be described in detail herein, the balloons 602 may be secured to one another, for example by heating or adhering for instance with an adhesive. As will also be described herein, one or more ports 606 may be formed to provide fluid communication to the chambers 604. As previously noted, where the balloons 602 are to be used with stents, the balloons 602 should have a length that is longer than a length of the stent, by an amount sufficient to accommodate axial movement between the balloons 602 when in a tortuous portion of a bodily vessel. As previously noted, the use of a plurality of balloons 602 individually having a smaller cross sectional area than a single balloon, which may move with respect to one another and/or which may be lubricous or carry a lubricant allows the expansion structure 600 to be more flexible than a single balloon expansion structure of similar size, providing numerous possible advantages.

Figure 7:
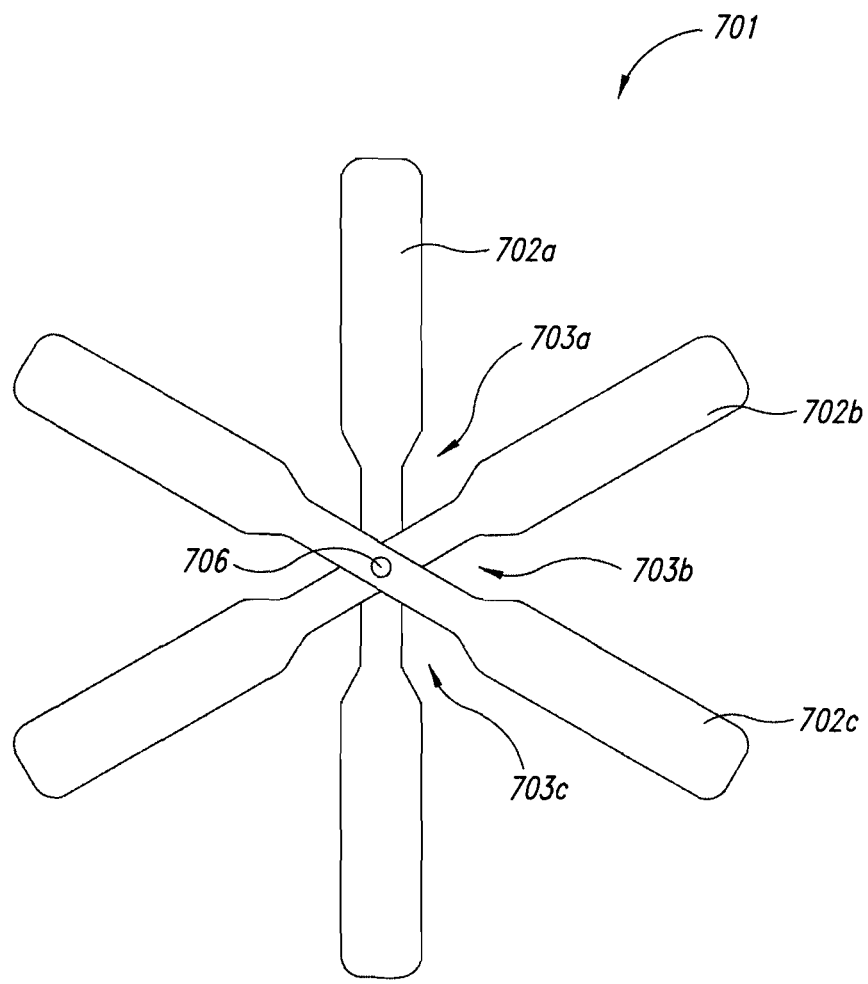
FIG. 7 is a top plan view of a plurality of necked balloon structures overlying one another to form a multi-balloon expansion structure, according to another illustrated embodiment.

FIG. 7 shows an expansion structure 700 according to another illustrated embodiment.

The expansion structure 700 may include a number of balloons 702a-702c (collectively 702). One or more of the balloons 702 may include a narrow or necked region or portion 703a-703c (collectively 703). The necked portion may be located between end portions thereof. One or more ports 706 may provide fluid communication to chambers (not illustrated) of the respective balloons 702. As previously noted, where the balloons 702 are to be used with stents, the balloons 702 should have a length that is longer than a length of the stent, by an amount sufficient to accommodate axial movement between the balloons 702 when in a tortuous portion of a bodily vessel. As previously noted, the use of a plurality of balloons 702 individually having a smaller cross sectional area than a single balloon, which may move with respect to one another and/or which may be lubricous or carry a lubricant allows the expansion structure 700 to be more flexible than a single balloon expansion structure of similar size, providing numerous possible advantages.

Figure 8A:
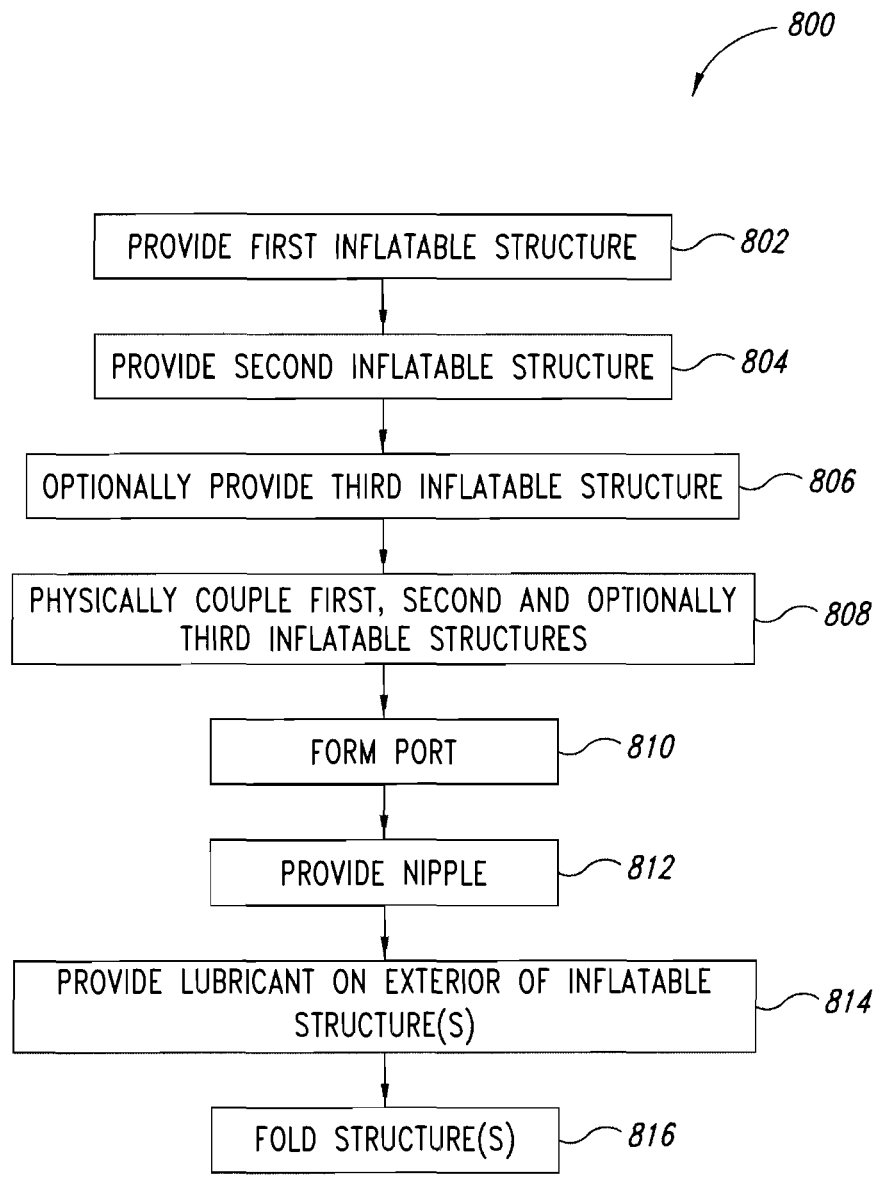
FIG. 8A is a flow diagram illustrating a method of forming a multi-balloon expansion structure according to one illustrated embodiment.

FIG. 8A shows a method 800 of forming an expansion structure, according to one illustrated embodiment.

At 802, a first inflatable structure is provided. At 804, a second inflatable structure is provided. Optionally at 806, one or more additional inflatable structures may be provided. The inflatable structures may take a variety of forms, for example any of the stent expanding type balloons previously described. The balloons may, for example, be laid over one another, for example as illustrated in FIGS. 6A, 6B and 7.

At 808, the inflatable structures are physically coupled to one another. The balloons may, for example, be physically coupled in or proximate a center region or portion, that is located between opposed end regions or portions.

At 810, one or more ports are formed to provide fluid communication to the interior or chambers of the inflatable structures. Optionally at 812, a nipple may be provided at the port. The nipple may facilitate fluid communicative coupling with the lumen(s) of the flexible elongated member.

Optionally at 814, a lubricant (e.g., fluorocarbons such as TEFLON®, silicone grease, Molybdenum Disulfide or graphite) maybe provided on an exterior of one or more of the inflatable structures. The lubricant reduces friction between the inflatable structures, allowing the inflatable structures to slide over each other as the inflatable structures physically engage one another during inflation. Such enhances the ability of the expansion structure to conform to a tortuous portion of a bodily vessel. In some embodiments, the inflatable structures may be formed of a material that is inherently lubricious.

Optionally at 816, the inflatable structures are folded to provide a relatively small diameter for the expansion structure. As previously noted, balloons are made of inelastic material, hence do not appreciable stretch when inflated. Folding allows the balloons to have a relatively small profile or cross-section when uninflated to facilitate travel through vasculature, while still allowing the balloons to have a relatively large profile or cross-section when inflated, the profile or cross section when inflated being large enough to expand a stent so as to physically engage the wall of the bodily vessel. Balloons may be manually or automatically folded, for example by passing the balloon through a die.

Alternatively, the balloons may be blow molded into a form. In some embodiments, the balloons may be put into a form, inflated and heated.

FIG. 8B shows a method useful in forming the expansion structure, according to one illustrated embodiment.

At 820, one or more inflatable structures having a neck portion may be provided. An example of such necked inflatable structures is illustrated in FIG. 7. Such may be employed to perform acts 802, 804, and/or 806 of the method 800.

FIG. 8C shows a method useful in forming the expansion structure according to one illustrated embodiment.

At 822, one or more of the inflatable structures may be heated to physically couple the inflatable structures to or more of the other inflatable structures. The heat may, for example, be applied to a center portion located between two opposed end portions of the inflatable structure. Heating may be employed to perform act 808 of the method 800.

FIG. 8D shows method useful in forming an expansion structure according to another illustrated embodiment.

At 824, one or more of the inflatable structures may be adhered to one or more of the other inflatable structures, for example using an adhesive. The adhesive may, for example, be applied to a center portion located between two opposed end portions of the inflatable structure. Adhering may be used to perform 808 of the method 800.

FIG. 8E shows a method useful in forming an expansion structure according to another illustrated embodiment.

At 826, one or more throughholes may be formed in one or more of the inflatable structures. The throughhole may be formed, for example, by laser drilling or plasma etching, or application of heat or electrical current. A single throughhole may extend to the chambers or interior of each of the inflatable structures, or separate throughholes may be employed for respective ones of the inflatable structures. Forming a throughhole may be used to perform act 810 of the method 800.

Figure 9:
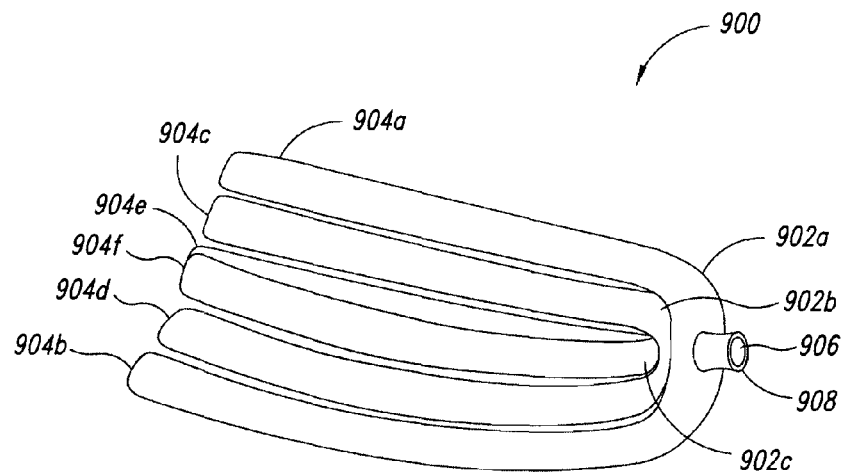
FIG. 9 is an isometric view of an expansion structure formed from a plurality of inflatable balloons and a port, according to one illustrated embodiment.

FIG. 9 shows an expansion structure 900 according to a further illustrated embodiment.

The expansion structure 900 includes three inflatable structures such as balloons 902a-902c (collectively 902). The balloons 902 are physically coupled to one another around a central portion, each having two fingers or legs 904a-904f (collectively 904) that may extend generally parallel to one another. The ends of the fingers or legs 904 is able to move with respect to one another. Where the balloons 902 are to be used with stents, the balloons 902 should have a length that is longer than a length of the stent, by an amount sufficient to accommodate axial movement between the balloons 902 when in a tortuous portion of a bodily vessel. The use of a plurality of balloons 902 and/or a plurality of fingers or legs 904, each individually having a smaller cross sectional area than a single balloon of a similar size as the collection of fingers or legs 904, which may move with respect to one another and/or which may be lubricous or carry a lubricant allows the expansion structure 900 to be more flexible than a single balloon expansion structure of similar size, providing numerous possible advantages.

The balloons 902 each include one or more interiors or chambers. The expansion structure 900 includes a port 906 and nipple 908 to provide fluid communication to the interior or chambers of the balloons 902. The nipple may facilitate a fluid communicative coupling with one or more lumens of a flexible elongated member. As noted with respect to previous embodiments, the balloons 902 may be inflated from a relatively uninflated state or configuration into a relatively inflated state or configuration by providing fluid to the interior of the balloons via the lumen.

Also as noted with respect to previous embodiments, the balloons 902 may be made of inelastic material and hence do not appreciably stretch. Thus, one or more of the fingers or legs 904 of the balloons 902 may be in a folded configuration when uninflated, which provides a cross section having a relatively small or reduced diameter for travel through the bodily vessel to the desired position. In response to inflation, the finger or legs 904 unfold into the relatively inflated state or configuration. In some embodiments, the balloons 902 may be elastic, appreciably stretching when inflated. In such embodiments the balloons 902 may or may not be folded since the profile or cross-section of the balloons 902 will be relatively small when uninflated versus when inflated. The balloons 902 may also be deflated, allowing removal of the balloons 902, for example after the balloons 902 have expanded a stent.

Individual fingers or legs 904 of the balloons 902 when expanded or unfolded may have a generally circular undeformed cross section. Such balloons are advantageously easy and inexpensive to manufacture as compared to more complex geometries. Where two or more of the fingers 904 of the balloons 902 are grouped together, neighboring fingers or legs 904 may physically interfere with one another as the balloons 902 inflate and unfold. Thus, the fingers or legs 904 which might otherwise have a circular cross section may assume a wedge or pie shape cross section, best illustrated in FIG. 10B. Notably, an outer perimeter portion of each of the fingers or legs 904 is approximately arcuate, and the group of fingers or legs 904 form a substantially circular cross section.

Figure 10A:
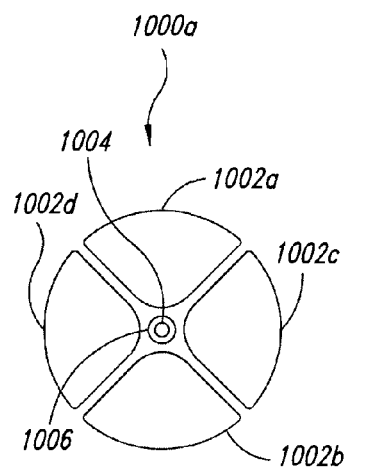
FIG. 10A is a front view showing an expansion structure formed of four inflatable balloons, according to one illustrated embodiment.

FIG. 10A shows an expansion structure 1000a, according to one illustrated embodiment.

The expansion structure 1000a is formed by two balloons each having two fingers or legs 1002a-1002d. Where the balloons are to be used with stents, the balloons should have a length that is longer than a length of the stent, by an amount sufficient to accommodate axial movement between the fingers or legs 1002a-1002d of the balloons when in a tortuous portion of a bodily vessel. The use of a plurality of balloons and/or a plurality of fingers or legs 1002a-1002d, each individually having a smaller cross sectional area than a single balloon of a similar size as the collection of fingers or legs 1002a-1002d, which may move with respect to one another and/or which may be lubricous or carry a lubricant allows the expansion structure 1000a to be more flexible than a single balloon expansion structure of similar size, providing numerous possible advantages.

An interior or chamber of each of the fingers or legs 1002a-1002d may be fluidly coupled to a lumen 1004 of a flexible elongated member 1006. Such allows selective inflation of the fingers or legs 1002a-1002d. As noted above, individual fingers or legs 1002a-1002d when expanded or unfolded may have a generally circular undeformed cross section. Such balloons are advantageously easy and inexpensive to manufacture as compared to more complex geometries. Where two or more of the fingers or legs 1002a-1002d are grouped together, neighboring fingers or legs 1002a-1002d may physically interfere with one another as the fingers or legs 1002a-1002d inflate and unfold. Thus, the fingers or legs 1002a-1002d which might otherwise have a circular cross section may assume a wedge or pie shape cross section. Notably, an outer perimeter portion of each of the fingers or legs 1002a-1002d is approximately arcuate, and the group of fingers or legs 1002a-1002d form a substantially circular cross section.

Figure 10C:
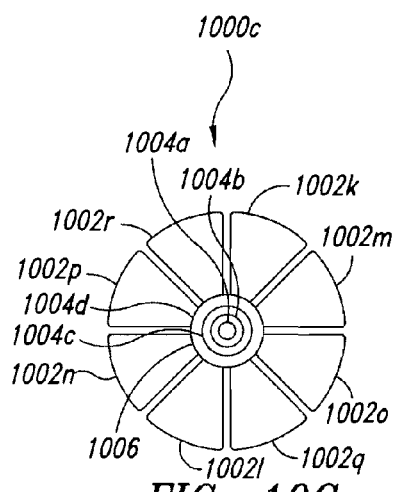
FIG. 10C is a front view of an expansion structure formed of eight inflatable balloons, according to another illustrated embodiment.
Figure 10B:
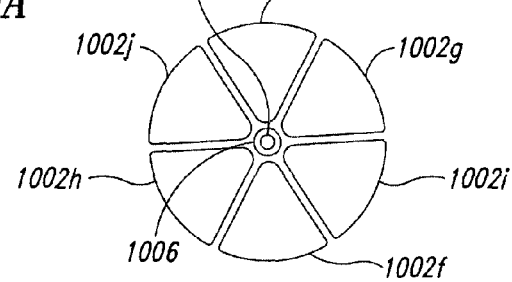
FIG. 10B is a front view of an expansion structure formed of six inflatable balloons, according to one illustrated embodiment.

FIG. 10B shows an expansion structure 1000b, according to one illustrated embodiment.

The expansion structure 1000b is formed from three balloons each having two respective fingers or legs 1002e-1002j. Where the balloons are to be used with stents, the balloons should have a length that is longer than a length of the stent, by an amount sufficient to accommodate axial movement between the fingers or legs 1002e-1002j of the balloons when in a tortuous portion of a bodily vessel. The use of a plurality of balloons and/or a plurality of fingers or legs 1002e-1002j, each individually having a smaller cross sectional area than a single balloon of a similar size as the collection of fingers or legs 1002e-1002j, which may move with respect to one another and/or which may be lubricous or carry a lubricant allows the expansion structure 1000b to be more flexible than a single balloon expansion structure of similar size, providing numerous possible advantages.

As previously noted, an interior of each of the fingers or legs 1002e-1002j may be fluidly communicatively coupled to a lumen 1004 of a flexible elongated member 1006. Also as previously noted individual fingers or legs 1002e-1002j when expanded or unfolded may have a generally circular undeformed cross section. Such balloons are advantageously easy and inexpensive to manufacture as compared to more complex geometries. Where two or more of the fingers or legs 1002e-1002j are grouped together, neighboring fingers or legs 1002e-1002j may physically interfere with one another as the fingers or legs 1002e-1002j inflate and unfold. Thus, the fingers or legs 1002e-1002j which might otherwise have a circular cross section may assume a wedge or pie shape cross section. Notably, an outer perimeter portion of each of the fingers or legs 1002e-1002j is approximately arcuate, and the group of fingers or legs 1002e-1002j form a substantially circular cross section. As previously noted, the fingers or legs 1002e-1002j may also be deflated, allowing removal of the expansion structure 1000b, for example after the expansion structure 1000b has expanded a stent.

FIG. 10c shows an expansion structure 1000c according to a further illustrated embodiment.

The expansion structure 1000c is formed from four balloons, each with two respective fingers or legs 1002k-1002p. Where the balloons are to be used with stents, the balloons should have a length that is longer than a length of the stent, by an amount sufficient to accommodate axial movement between the fingers or legs 1002k-1002p of the balloons when in a tortuous portion of a bodily vessel. The use of a plurality of balloons and/or a plurality of fingers or legs 1002k-1002p, each individually having a smaller cross sectional area than a single balloon of a similar size as the collection of fingers or legs 1002k-1002p, which may move with respect to one another and/or which may be lubricous or carry a lubricant allows the expansion structure 1000c to be more flexible than a single balloon expansion structure of similar size, providing numerous possible advantages.

As previously noted, an interior of each of the fingers or legs 1002k-1002p may be fluidly communicatively coupled to a lumen 1004 of a flexible elongated member 1006. Also as previously noted individual fingers or legs 1002k-1002p when expanded or unfolded may have a generally circular undeformed cross section. Such balloons are advantageously easy and inexpensive to manufacture as compared to more complex geometries. Where two or more of the fingers or legs 1002k-1002p are grouped together, neighboring fingers or legs 1002k-1002p may physically interfere with one another as the fingers or legs 1002k-1002p inflate and unfold. Thus, the fingers or legs 1002k-1002p which might otherwise have a circular cross section may assume a wedge or pie shape cross section. Notably, an outer perimeter portion of each of the fingers or legs 1002k-1002p is approximately arcuate, and the group of fingers or legs 1002k-1002p form a substantially circular cross section. As previously noted, the fingers or legs 1002k-1002p may also be deflated, allowing removal of the expansion structure 1000c, for example after the expansion structure 1000c has expanded a stent.

FIGS. 11A-11E show an expansion structure 1100 according to a further illustrated embodiment.

The expansion structure 1100 includes a balloon 1102 including a plurality of fingers or legs 1102a-1102g. The fingers or legs 1102 may extend substantially parallel to one another. A distal end 1103 of the fingers or legs 1102a-1102g are able to move with respect to one another. In particular, the distal ends 1103 may move axially with respect to one another. Where the balloons are to be used with stents, the balloons should have a length that is longer than a length of the stent, by an amount sufficient to accommodate axial movement between the fingers or legs 1102a-1102g of the balloons when in a tortuous portion of a bodily vessel. The use of a balloon with a plurality of fingers or legs 1102a-1102g, each individually having a smaller cross sectional area than a single balloon of a similar size as the collection of fingers 1102a-1102g, which may move with respect to one another and/or which may be lubricous or carry a lubricant allows the expansion structure 1100 to be more flexible than a single balloon expansion structure of similar size, providing numerous possible advantages.

As previously noted, an interior of each of the fingers or legs 1102a-1102g may be fluidly communicatively coupled to a lumen 1104 of a flexible elongated member (not shown in FIGS. 11A-11E). Also as previously noted individual fingers 1102a-1102g when expanded or unfolded may have a generally circular undeformed cross section. Such balloons 1102 are advantageously easy and inexpensive to manufacture as compared to more complex geometries. Where two or more of the fingers 1102a-1102g are grouped together, neighboring fingers 1102a-1102g may physically interfere with one another as the fingers 1102a-1102g inflate and unfold. Thus, the fingers 1102a-1102g which might otherwise have a circular cross section may assume a wedge or pie shape cross section. Notably, an outer perimeter portion of each of the fingers 1102a-1102g is approximately arcuate, and the group of fingers 1102a-1102g form a substantially circular cross section as best illustrated in FIG. 11E. As previously noted, the fingers 1102a-1102g may also be deflated, allowing removal of the expansion structure 1100, for example after the expansion structure 1100 has expanded a stent.

The balloon 1102 may be rolled such that the fingers 1102a-1102g form an approximately cylindrical structure. For example, with reference to FIG. 11B, fingers 1102a-1102c may be rolled counterclockwise with respect to finger 1102d and fingers 1102e-1102g may be rolled counterclockwise with respect to finger 1102d to form the structure illustrated in FIG. 11D.

FIG. 11D shows the expansion structure 1100 in a relatively uninflated state or configuration. Each finger 1102a-1102g may have an uninflated, unfolded circular cross section. When inflated, physical interaction between neighboring ones of the fingers 1102a-1102g cause the fingers 1102a-1102g to have an approximately wedge shape or pie-shaped cross section, best illustrated in FIG. 11E. Notably, an outer perimeter portion of each of the fingers 1102a-1102g is approximately arcuate, and the group of fingers 1102a-1102g have a substantially circular cross section.

The fingers 1102a-1102g may be formed of a lubricous material or may be at least partially covered by a lubricant. Such facilitates sliding movement between the fingers 1102a-1102g, particularly as the 1102a-1102g are inflated. In some embodiments, the sliding movement may occur up until a maximum inflated state or configuration, at which point the friction may prevent the fingers 1102a-1102g from moving with respect to one another.

Figure 12:
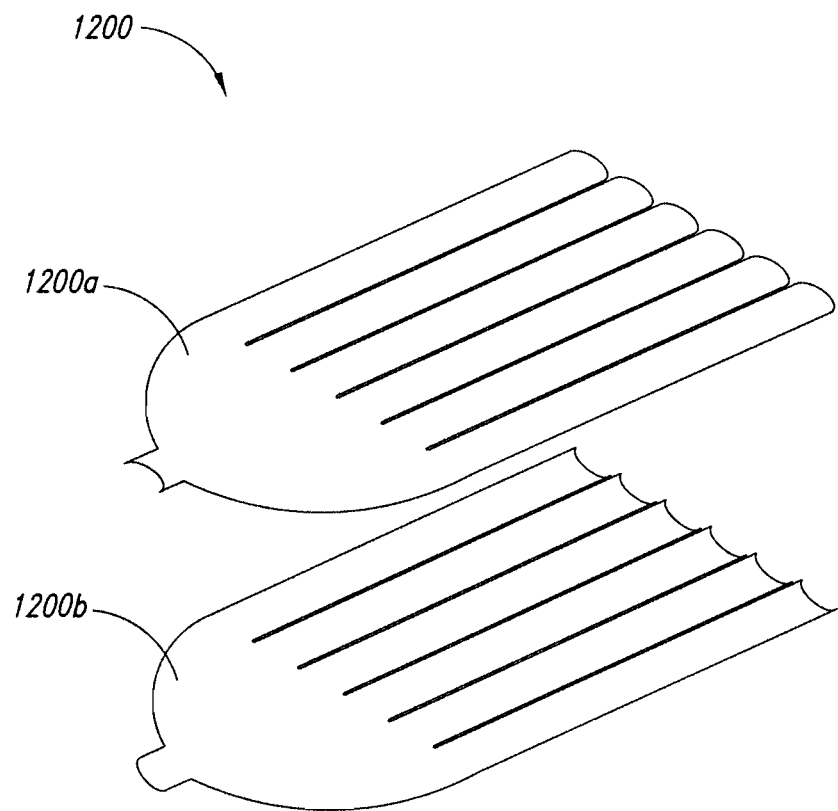
FIG. 12 is an isometric view of two portions which may be joined together to form the expansion structure of FIGS. 11A-11E.

FIG. 12 shows an expansion structure 1200, according to one illustrated embodiment.

The expansion structure 1200 may be formed of a first portion 1200a and a second portion 1200b. As described herein with reference to FIGS. 13A-13C, the portions 1200a, 1200b may be physically coupled to form a single balloon with multiple fingers, which may extend substantially parallel to one another. The expansion structure may be an inelastic material, similar to or the same as materials currently used in balloons for expanding stents.

Figure 13A:
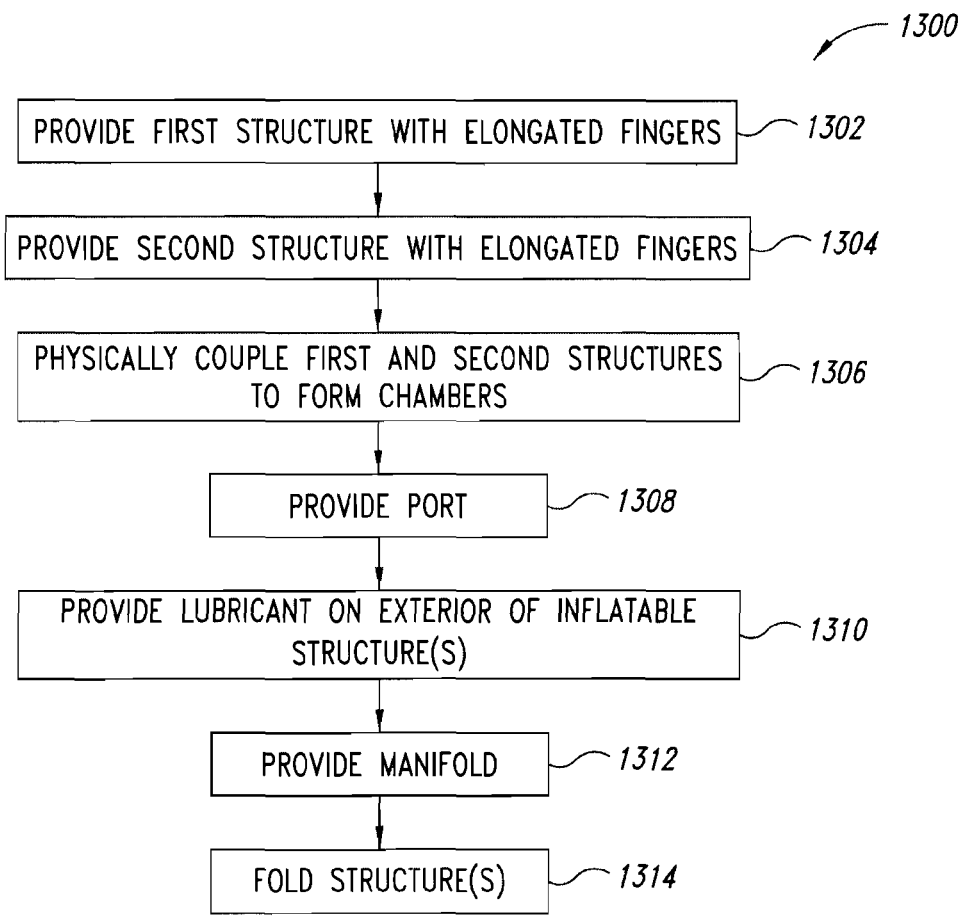
FIG. 13A is a flow diagram of a method of forming an expansion structure having multiple inflatable chambers, according to one illustrated embodiment.

FIG. 13A shows a method 1300 of forming an expansion structure similar to the one illustrated in FIG. 12, according to one illustrated embodiment.

At 1302, a first structure or portion with elongated fingers is provided. At 1304, at least a second structure or portion with elongated fingers is provided. At 1306, the first and second structures or portions are physically coupled to form one or more interiors or chambers.

At 1308, a port is provided. The port provides fluid communication with the interior or chambers of the elongated fingers.

Optionally at 1310, a lubricant may be provided on an exterior of the expansion structure, for example on one or more of the inflatable fingers. In some embodiments, the material of the first and second structures or portions may be inherently lubricious, hence a lubricant may not be employed. In still other embodiments, it may be possible to achieve sufficient movement between the fingers without either a lubricant or lubricious material.

At 1312, a manifold may be provided. The manifold may be physically coupled to the expansion structure, and one or more passages of the manifold may be coupled to provide fluid communication with the interior or chambers.

At 1314, the expansion structure may be folded. For example, the expansion structure may be folded to wrap one or more of the fingers to produce a generally cylindrical structure such as that of FIG. 11B. Additionally or alternatively, one or more of the fingers may be folded to reduce an overall cross sectional diameter of the resulting expansion structure, for example as illustrated in FIG. 3C.

Figure 13B:
FIG. 13B is a flow diagram of a method of physically securing the portions illustrated in FIG. 12, according to one illustrated embodiment.

FIG. 13B shows a method useful in forming the expansion structure according to another illustrated embodiment.

At 1316, at least one of the first and second structures or portions may be heated to physically couple the first and second structures. Such may be used to implement act 1306 of method 1300.

Figure 13C:
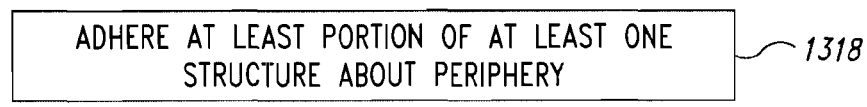
FIG. 13C is a flow diagram of a method of physically securing the portions of FIG. 12 according to another illustrated embodiment.

FIG. 13C shows a method useful in forming an expansion structure, according to another illustrated embodiment.

At 1318, the first and second structures or portions are physically adhered to one another, for example via an adhesive applied about the periphery of the first and/or second structures or portions.

FIGS. 14A-14D show an expansion structure 1400 according to another illustrated embodiment.

The expansion structure 1400 includes a single inflatable member such as a balloon 1402. The balloon 1402 includes a number of segments or portions 1402a-1402h formed by necks or bends in the balloon 1402. The segments or portions 1402a-1402h may be substantially parallel to one another. Where the balloons are to be used with stents, the segments or portions 1402a-1402h should have a length that is longer than a length of the stent, by an amount sufficient to accommodate axial movement between the segments or portions 1402a-1402h of the balloons when in a tortuous portion of a bodily vessel. The use of a balloon with a plurality of segments or portions 1402a-1402h, each individually having a smaller cross sectional area than a single balloon of a similar size as the collection of segments or portions 1402a-1402h, which may move with respect to one another and/or which may be lubricous or carry a lubricant allows the expansion structure 1400 to be more flexible than a single balloon expansion structure of similar size, providing numerous possible advantages.

Each segment or portion 1402a-1402h forms a respective interior of chambers 1404a-1404h. The chambers 1404a-1404h are serially coupled to one another to allow fluid communication therethrough. The balloon 1402 includes two ports 1406a, 1406b located at terminal ends 1408a, 1408b. The balloon 1402 may be inflated from a relatively uninflated state or configuration, best illustrated in FIG. 14D, into a relatively inflated state or configuration, best illustrated in FIG. 14E, by providing fluid to the interior or chambers 1404a-1404h of the balloon 1402 via the ports 1406a, 1406b. As previously noted, the segment or portion 1402a-1402h may also be deflated, allowing removal of the expansion structure 1400, for example after the expansion structure 1400 has expanded a stent.

As best illustrated in FIG. 14C, the balloon 1402 may be folded such that the balloon 1402 has the approximately circular cross section illustrated in FIG. 14D. For example, a section 1402k of the balloon 1402 may be folded counter-clockwise to form an approximately right angle with respect to a section 1402f, and a section 1402l may be then folded counterclockwise to form an approximately right angle with respect to the section 1402g, thus being approximately parallel with the section 1402j. Further, a section 1402i of the balloon 1402 may be folded clockwise with respect to the section 1402b to form an approximately right angle thereto. The folded balloon 1402 is illustrated in FIG. 14D in an uninflated state or configuration. The folded balloon 1402 is illustrated in FIG. 14E in the inflated configuration. Thus, the segments or portions 1402a-1402h of the balloon 1402 which might otherwise have a circular cross section may have a wedge or pie shape cross section, best illustrated in FIG. 14E. Notably, an outer perimeter portion of each of the segments or portions 1402a-1402h is approximately arcuate, and the group of segments or portions 1402a-1402h have a substantially circular cross section.

Additionally or alternatively, one or more of the segments or portions 1402a-1402h may be folded to reduce an overall cross sectional diameter of the resulting expansion structure 1400, for example in a manner similar to that as illustrated in FIG. 3C.

Figure 15A:
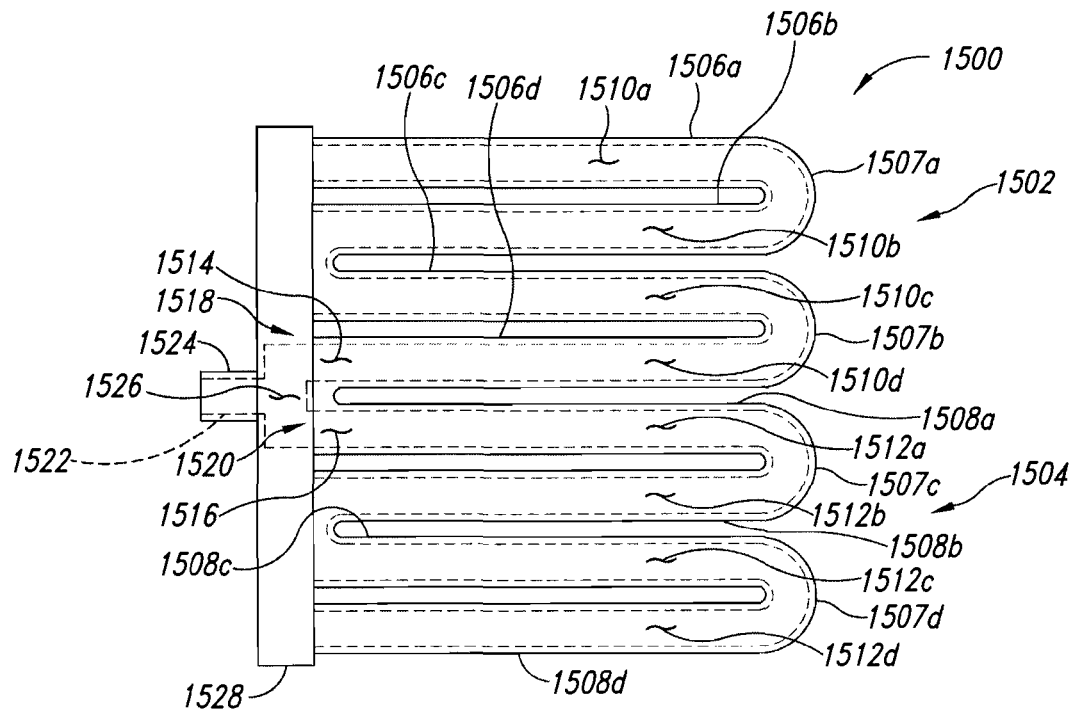
FIG. 15A is a top plan elevational view of a catheter device including a flexible elongated member, a manifold and two multi-chambered inflatable structures in an unfolded configuration, according to one illustrated embodiment.
Figure 15B:
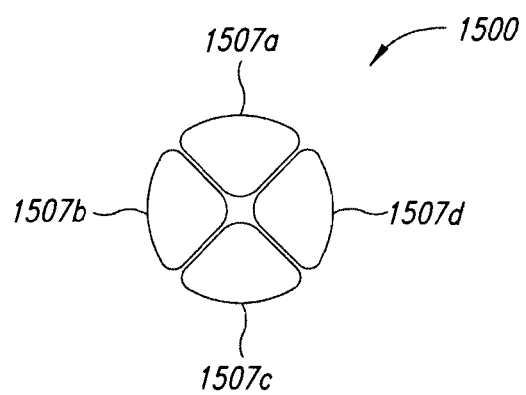
FIG. 15B is an end view of the device of FIG. 15A in an inflated state or configuration, where a structure that forms a number of outer ones of the chambers is wrapped around a structure that forms an inner one of the chambers, according to one illustrated embodiment.

FIGS. 15A and 15B show an expansion structure 1500 according to a further illustrated embodiment.

The expansion structure 1500 includes two inflatable members such as a balloons 1502, 1504. The balloons 1502, 1504 each includes a number of segments or portions 1506a-1506d, 1508a-1508d formed by necks or bends in the balloons 1502, 1504. The segments or portions 1506a-1506d, 1508a-1508d may be substantially parallel to one another. Where the balloons are to be used with stents, the segments or portions 1506a-1506d, 1508a-1508d should have a length that is longer than a length of the stent, by an amount sufficient to accommodate axial movement between the segments or portions 1506a-1506d, 1508a-1508d of the balloons when in a tortuous portion of a bodily vessel. The use of a plurality of balloons 1502, 1504 and/or a plurality of segments or portions 1506a-1506d, 1508a-1508d, each individually having a smaller cross sectional area than a single balloon of a similar size as the collection of segments or portions 1506a-1506d, 1508a-1508d, which may move with respect to one another and/or which may be lubricous or carry a lubricant allows the expansion structure 1500 to be more flexible than a single balloon expansion structure of similar size, providing numerous possible advantages.

Each segment or portion 1506a-1506d, 1508a-1508d forms a respective interior of chambers 1510a-1510d, 1512a-1512d. For each balloon 1502, 1504, the chambers 1510a-1510d, 1512a-1512d are serially coupled to one another to allow fluid communication therethrough. Each of the balloons 1502, 1504 includes ports 1514, 1516 located at terminal ends 1518, 1520. The ports 1514, 1516 may be fluidly communicatively to a lumen 1522 of a flexible elongated member 1524 by one or more passages 1526 of a manifold 1528. The balloons 1502, 1504 may be inflated from a relatively uninflated state or configuration, into a relatively inflated state or configuration, best illustrated in FIG. 15B, by providing fluid to the interior or chambers 1510a-1510d, 1512a-1512d of the balloons 1502, 1504. As previously noted, the segment or portion 1506a-1506d, 1508a-1508d may also be deflated, allowing removal of the expansion structure 1500, for example after the expansion structure 1500 has expanded a stent.

As with the previously described embodiments, segments 1507a-1507d of the balloons 1502, 1504 may be folded or wrapped with respect to each other to achieve a structure which will have a cross section with an outer diameter that is substantially circular when inflated, as best illustrated in FIG. 15B.

Additionally or alternatively, one or more of the segment or portion 1506a-1506d, 1508a-1508d may be folded to reduce an overall cross sectional diameter of the resulting expansion structure 1500, for example in a manner similar to that as illustrated in FIG. 3C.

Figure 16:
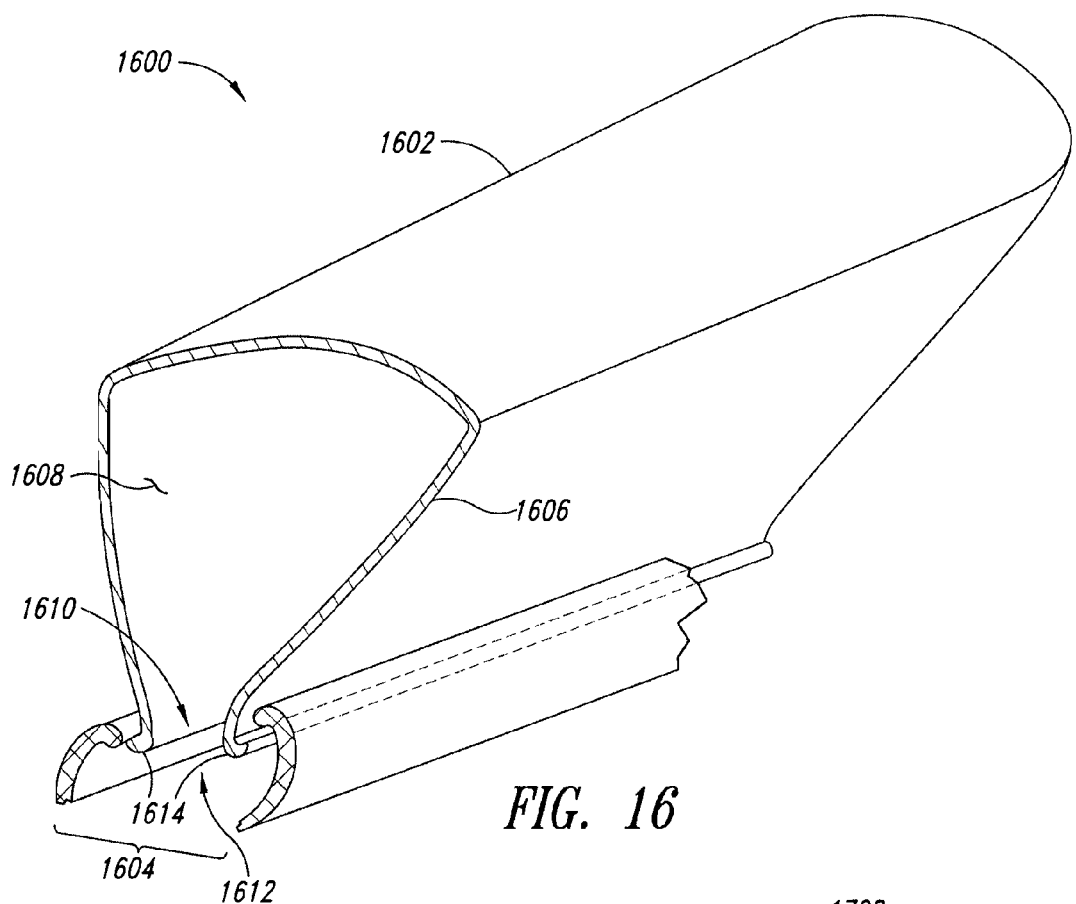
FIG. 16 is a partially broken view of an inflatable structure secured to a support structure such as a flexible elongated member of a catheter having fluid communication with a lumen of flexible elongated member, according to one illustrated embodiment.

FIG. 16 shows a portion of an expansion structure 1600 according to one illustrated embodiment.

The expansion structure 1600 includes at least one inflatable structure such as a balloon 1602 and a support structure 1604 to which the balloon 1602 is physically coupled.

The balloon 1602 has at least one wall 1606 that forms an interior or chamber 1608. A port 1610 may provide fluid communication with the interior or chamber 1608. The balloon 1602 may be inflated from a relatively uninflated state or configuration into a relatively inflated state or configuration by providing fluid to the interior or chambers 1608 of the balloon 1602. As previously noted, the balloon 1602 may be made of inelastic material, and hence may be folded in an uninflated state or configuration, and unfolded in an inflated state or configuration. The balloon 1602 may also be deflated, allowing removal of the balloon 1602, for example after the balloon 1602 has expanded a stent.

The support structure 1604 may take a variety of forms, for example one or more elongated flexible members, which may, for instance, form part of a catheter device. The support structure 1604 includes at least one opening 1612 providing fluid communication with the interior or chamber 1608 of the balloon 1602. In one embodiment, the opening 1612 extends along a substantial length of the balloon 1602, for example greater than 25% of the length of the balloon 1602.

The balloon 1602 may be physically coupled to the support structure 1604 by any of a variety of attachment mechanisms 1614. For example, the attachment mechanism may take the form of one or more lips, such as the illustrated interlocking lips, lip and bead, or groove and tongue. Other attachment mechanisms 1614 may include adhesives.

Figure 17:
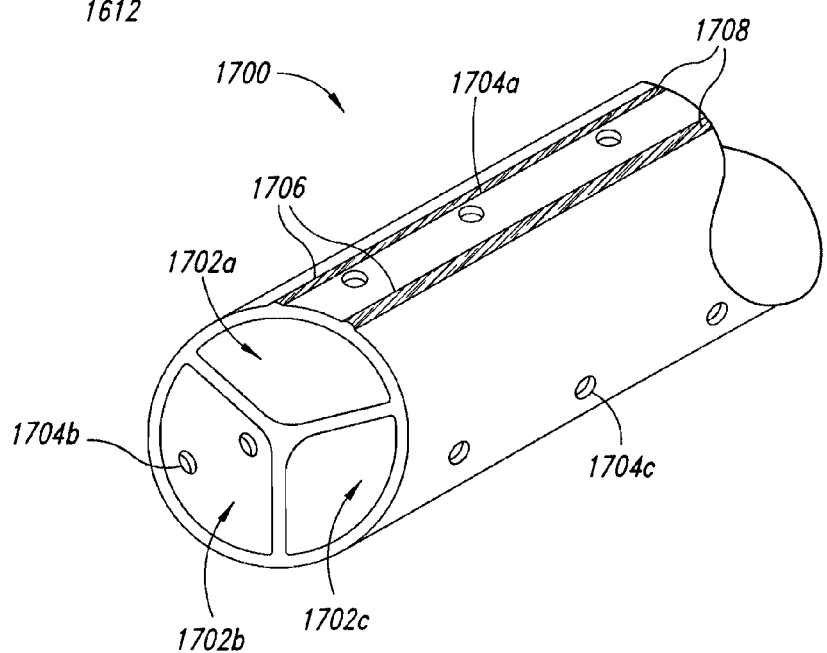
FIG. 17 is an isometric view of a portion of a multi-lumen flexible elongated member of a catheter, including ports for providing fluid communication with three inflatable structures, according to one illustrated embodiment.

FIG. 17 shows a portion of a support structure 1700 according to one illustrated embodiment.

The support structure 1700 may take the form of a flexible elongated member, which may, for instance, form part of a catheter device. The support structure 1700 may include one or more lumens, for example the three lumens 1702a-1702c illustrated in FIG. 17. In some embodiments, the lumens may be concentrically disposed with respect to one another, for example as indicated in FIG. 10C.

The support structure 1700 has one or more ports 1704a-1704c (only three called out in FIG. 17) that provide fluid communication between the lumens 1702a-1702c and respective inflatable structures (not illustrated in FIG. 17), for example the balloon 1602 (FIG. 16). The support structure 1700 may include suitable attachment mechanism 1706, for example a rigid on which the inflatable structure may be secured via an adhesive 1708.

Figure 18:
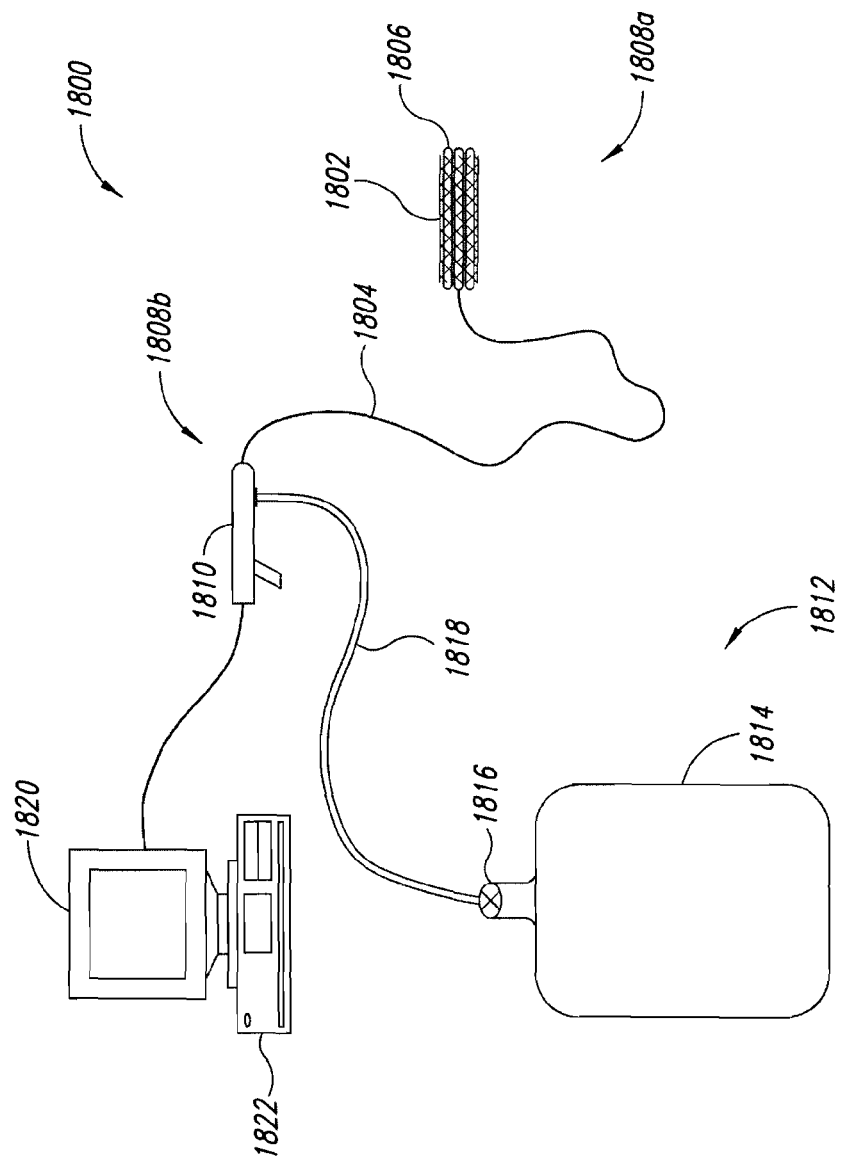
FIG. 18 is a schematic diagram of a catheter system according to one illustrated embodiment, include a catheter device, fluid control subsystem and an imaging subsystem.

FIG. 18 shows a catheter system 1800, according to one illustrated embodiment.

The catheter system 1800 is operable to position and expand a stent 1802 percutaneously in vasculature. The catheter system 1800 includes at least one flexible elongated member 1804 and an expansion structure 1806 positioned at least proximate a distal end 1808a thereof.

As previously noted, the flexible elongated member 1804 may include one or more lumens. The flexible elongated member 1804 may, for example, comprise a portion of a catheter device.

The expansion structure 1806 may take any of a variety of forms, for example one of the expansion structures previously described, which allow travel through torturous vasculature. The expansion structure 1806 may, for example, allow for the positioning and/or implantation of the stent 1802 in the vasculature. Alternatively, or additionally, expansion structure 1806 may, for example, allow for the elimination of blockages via angioplasty techniques.

The catheter system 1800 may include a tool 1810 to which a proximate end 1808b of the flexible elongated member 1804 is coupled. The tool 1810 is operable by a care provider to guide the flexible elongated member 1804 through the vasculature and/or to cause inflation and/or cause deflation of the expansion structure 1806. Those of skill in the art will recognized any of a variety of tools 1810 may be employed.

The tool 1810 typically has an integral inflation subsystem that includes a pump, valve and reservoir of fluid such as a saline solution for inflating the balloon. FIG. 18 shows an inflation subsystem 1812 illustrated separately from the tool 1810 for ease of presentation and discussion. Most embodiments will incorporate such elements into the tool 1810 itself.

The catheter system 1800 includes an inflation subsystem 1812. The inflation subsystem 1812 may take a variety of forms that are operable to provide a pressurized fluid. The inflation subsystem 1812 may include a fluid reservoir 1814. The fluid reservoir 1814 may store fluid under pressure. Alternatively, the fluid reservoir 1814 may store fluid and one or more pumps or compressors used to pressurize the fluid prior to delivery to the expansion structure 1806. The fluid may take a variety of forms, although will typically be in a liquid form to achieve a high degree of incompressibility. However, it is noted that the fluid may take a gaseous form in some embodiments. The fluid may, for example, take the form of saline and iodine liquid at a 1:1 ratio. Using liquids with lower viscosity may allow for faster inflation and deflation, reducing the amount of time that the balloons occlude the vessel.

The inflation subsystem 1812 may include a valve 1816 that is operable to control a supply of fluid to the tool 1814. The valve 1816 may be manually operable or may be automatically operable, for example a valve driven by a solenoid. The inflation subsystem 1812 may include one or more conduits 1818 that fluid communicatively couples the fluid reservoir 1814 to the tool 1810, and hence to one or more lumens of the flexible elongated member 1804. As previously noted, one or more of the fluid reservoir 1814, valve 1816 or other elements of the inflation subsystem 1812 may be integrated into the tool 1810.

The catheter system 1800 may further include additional subsystems that facilitate operation and/or guidance and/or placement of the flexible elongated member 1804 and/or expansion structure 1806 and/or expansion of the same. For example, the catheter system 1800 may include one or more monitors 1820 to allow a caregiver to visually monitor the position of the catheter 1804 in the vasculature. In such an embodiment, the flexible elongated member 1804 will carry one or more cameras, which may provide image data to a computing or processing system 1822 via one or more wired or wireless communications channels. The computing or processing system 1822 may include one or more processors, for example, microprocessors, digital signal processors, application specific integrated circuits and field programmable gate arrays, and may include one or more computer-readable memories, for example hard disks, optical disks, floppy disks, read only memory (ROM) and random access memory (RAM) to name a few. The computer-readable memories may store instructions that cause the processors to display an image on the display 1820 and/or control one or more other aspects of the catheter system 1800, for instance the valve 1816, FIG. 19 an expansion structure 1900, a stent 1902 and a cap 1904, according to another illustrated embodiment.

In at least some embodiments where the balloons 1906a-1906c (collectively 1906) are to be used to expand a stent 1902, the balloons 1906 or portions (e.g., fingers, legs, segments) thereof should have a length $L_B$ that is longer than a length $L_S$ of the stent 1902, by an amount sufficient to accommodate axial movement between the balloons or portions thereof when in a tortuous portion of a bodily vessel. The length $L_B$ of the balloons 1906 may, for example, be greater than the length $L_s$ of the stent 1902 by an amount equal to pi times the largest radius of curvature to be encountered in the bodily vessel. In some embodiments, the length $L_B$ of the balloons 1906 may, for example, be greater than the length $L_S$ of the stent 1902 by an amount equal to pi times the sum of the largest radius of curvature to be encountered in the bodily vessel and a contraction length indicative of an amount of contraction experience by the balloons 1906 as the balloons 1906 inflate.

The cap 1904 may temporarily radially retains the distal ends 1908a-1908c (collectively 1908) of the balloons 1906, which are otherwise able to move with respect to one another.

Figure 20A:
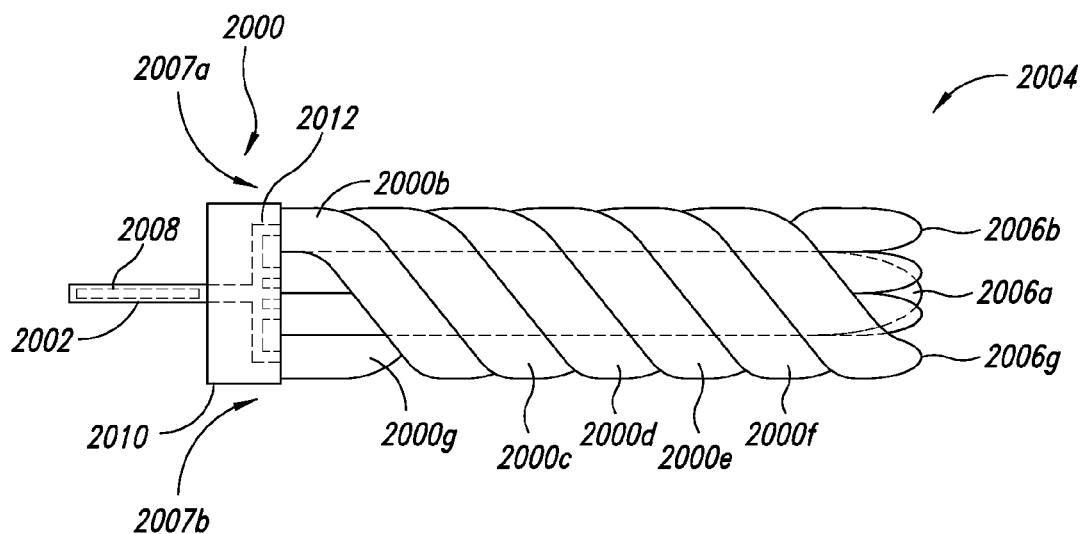
FIG. 20A is a side elevational view of a catheter device including a flexible elongated member, a manifold, and an expansion structure formed by a plurality of inflatable structures helically wound with respect to an axis, according to one illustrated embodiment.
Figure 20B:
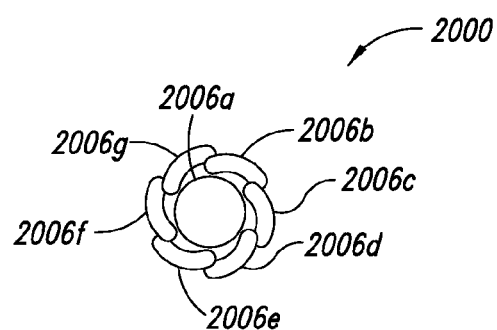
FIG. 20B is a front elevational view of the device of FIG. 4A, showing the inflatable structures in an uninflated state or configuration, according to one illustrated embodiment.

FIGS. 20A and 20B show a catheter device 2000, according to another illustrated embodiment.

The catheter device 2000 includes a flexible elongated member 2002 and an expansion structure 2004 positioned at least proximate one end of the flexible elongated member 2002. The expansion structure 2004 includes a plurality of peripheral inflatable structures such as balloons 2006a-2006f arranged around a central inflatable structure such as balloon 2006g (collectively 2006). The balloons 2006 may be helically wound or positioned with respect to a central axis along which balloon 2006g is positioned; the number of turns in the helix may be anywhere from a half turn (such as is shown in FIGS. 20A and 20B) up to an upper limit as permitted by the material(s) employed in the manufacture of the inflatable structures and dimensions thereof without loss of integrity of the device. A first end 2007a of the balloons are secured with respect to one another, while a second end 2007b of the balloons are able to move with respect to one another. In particular, the ends 2007b may move axially with respect to one another. As previously noted, where the balloons 2006 are to be used with stents, the balloons 2006 should have a length that is longer than a length of the stent, by an amount sufficient to accommodate axial movement between the balloons 2006 when in a tortuous portion of a bodily vessel. As previously noted, the use of a plurality of balloons 2006 individually having a smaller cross sectional area than a single balloon, which may move with respect to one another and/or which may be lubricous or carry a lubricant allows the expansion structure 2004 to be more flexible than a single balloon expansion structure of similar size, providing numerous possible advantages.

The inflatable structures 2006 include interiors or chambers which may be fluidly communicatively coupled to one or more lumens 2008 of the flexible elongated member 2002 by one or more manifolds 2010. Passages 2012 in the manifold 2010 are illustrated in broken line. The inflatable structures 2006 in FIGS. 20A and 20B are illustrated in a relatively uninflated state or configuration. Inflation of the inflatable structures 2006 will, to at least some extent, unwind the helical structure. As noted previously, the inflatable structures 2006 may be inelastic and do not appreciably stretch even under relatively high pressures associated with balloons that expand stents. Thus, one or more of the inflatable structures 2006 may in a folded configuration in the relatively uninflated state or configuration to reduce an overall diameter of a cross section of the expansion structure 2004 for travel through the bodily vessel. In some embodiments, the inflatable structures 2006 are elastic, appreciably stretching when inflated. In such embodiments the inflatable structures 2006 may or may not be folded since the profile or cross-section of the inflatable structures 2006 will be relatively small when uninflated versus when inflated. The inflatable structures 2006 may also be deflated, allowing removal of the inflatable structures 2006, for example after the inflatable structures 2006 have expanded a stent.

Figure 21:
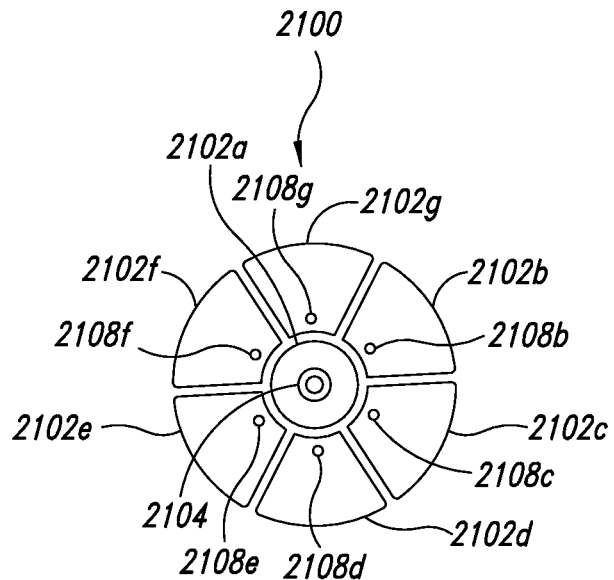
FIG. 21 is a front view of an expansion structure formed of seven inflatable balloons, according to one illustrated embodiment.

FIG. 21 shows an expansion structure 2100, according to one illustrated embodiment.

The expansion structure 2100 includes a plurality of peripheral inflatable structures such as balloons 2102b-2102g arranged around a central inflatable structure such as balloon 2102a (collectively 2102). Where the inflatable structures are to be used with stents, the inflatable structures should have a length that is longer than a length of the stent, by an amount sufficient to accommodate axial movement between the inflatable structures 2102 of the when in a tortuous portion of a bodily vessel. The use of a plurality of balloons and/or a plurality of inflatable structures 2102, each individually having a smaller cross sectional area than a single balloon of a similar size as the collection of inflatable structures 2102, which may move with respect to one another and/or which may be lubricous or carry a lubricant allows the expansion structure 2100 to be more flexible than a single balloon expansion structure of similar size, providing numerous possible advantages.

An interior or chamber of each of the inflatable structures 2102 may be fluidly coupled by an inflation port 2108 to a lumen 2104 of a flexible elongated member 2106, which may allow selective inflation of the inflatable structures 2102. For each peripheral inflatable structures 2102b-2102g, each respective inflation port 2108b-2108g is positioned eccentrically, closer to the central inflatable structure 2102a rather than at the center of each such peripheral inflatable structure 2102b-2102g. Such eccentric positioning of the inflation ports in the peripheral inflatable structures permits the cross profile of the expansion structure in its uninflated state to remain smaller than it would be if the inflation ports of the peripheral inflatable structures were located centrally or towards the outer perimeter of the peripheral inflatable structures. In respect of the central inflatable structure, the location of the inflation port may be central or it may be eccentric. As noted above, individual inflatable structures 2102 when expanded or unfolded may have a generally circular undeformed cross section. Where two or more of the inflatable structures 2102 are grouped together, neighboring inflatable structures 2102 may physically interfere with one another as the inflatable structures 2102 inflate and unfold. Thus, the inflatable structures 2102 which might otherwise have a circular cross section may assume a wedge or pie shape cross section. Notably, an outer perimeter portion of each of the peripheral inflatable structures 2102b-2102g is approximately arcuate, and the group of inflatable structures 2102 form a substantially circular cross section. As previously noted, the inflatable structures 2102 may also be deflated, allowing removal of the expansion structure 2100, for example after the expansion structure 2100 has expanded a stent.

Figure 22:
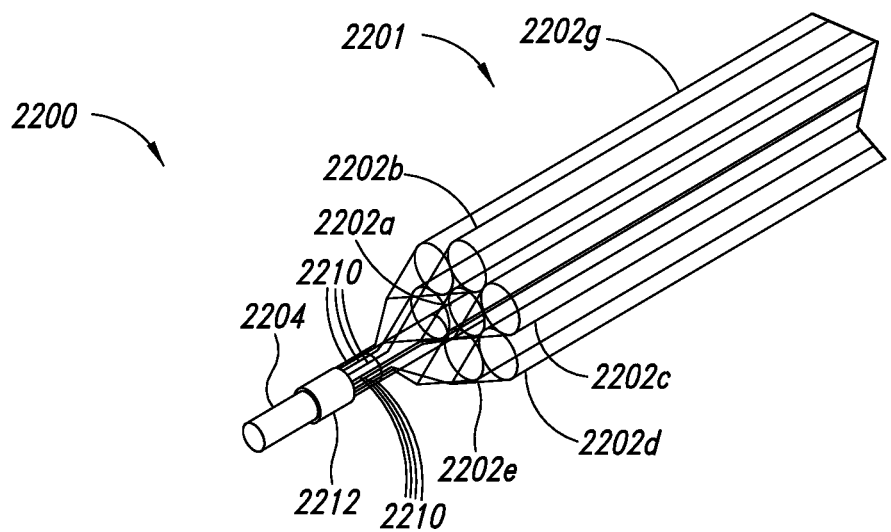
FIG. 22 is a perspective view of a distal end of a catheter device including a flexible elongated member, an expansion structure formed by a plurality of inflatable structures, inflatable structure restraints, and a restraint housing.

FIG. 22 shows a distal end of a catheter device 2200, according to one illustrated embodiment.

The expansion structure 2201 includes a plurality of peripheral inflatable structures such as balloons 2202b-2202g arranged around a central inflatable structure such as balloon 2202a (collectively 2202). Where the balloons are to be used with stents, the balloons should have a length that is longer than a length of the stent, by an amount sufficient to accommodate axial movement between the inflatable structures 2202 when in a tortuous portion of a bodily vessel. The use of a plurality of inflatable structures 2202, each individually having a smaller cross sectional area than a single balloon of a similar size as the collection of inflatable structures 2202, which may move with respect to one another and/or which may be lubricous or carry a lubricant allows the expansion structure 2200 to be more flexible than a single balloon expansion structure of similar size, providing numerous possible advantages.

As previously noted, an interior of each of the inflatable structures 2202 may be fluidly communicatively coupled to a lumen of a flexible elongated member 2204. Also as previously noted individual inflatable structures 2202 when expanded or unfolded may have a generally circular undeformed cross section. Where two or more of inflatable structures 2202 are grouped together, neighboring inflatable structures 2202 may physically interfere with one another as the inflatable structures 2202 inflate and unfold. Thus, the inflatable structures 2202 which might otherwise have a circular cross section may assume a wedge or pie shape cross section. As previously noted, the inflatable structures 2202 may also be deflated, allowing removal of the expansion structure 2201, for example after the expansion structure 2201 has expanded a stent.

In addition, the expansion structure 2201 is slidably anchored to a restraint housing 2212 mounted on flexible elongated member 2204 by restraints 2210, which prevents the distal ends of peripheral inflatable structures 2202b-2202g from flaring away from flexible elongated member 2204 and potentially into the walls of the body lumen or vessel into which catheter device 2200 may be deployed. Restraints 2204 engage the distal ends of inflatable structures 2202b-2202g with restraint housing 2212. Restraint housing 2212 permits movement of the portion of each restraint 2204 in restraint housing 2212 along a path in the housing, but constrains distal ends of the restraints 2204 from becoming free of the housing 2212. Housing 2212 and restraints 2210 thus permit longitudinal flexibility of the inflatable members relative to one another during radial expansile motion. Restraints may be separate elements attached at their proximal ends to the inflatable structures, or they may be extensions of the inflatable structures themselves. In addition, other embodiments may further include such restraints and restraint housings; their use is not limited to expansion structure illustrated in FIG. 22.

The above description of illustrated embodiments, including what is described in the Abstract, is not intended to be exhaustive or to limit the embodiments to the precise forms disclosed.

Some suitable materials for the various inflatable structures or balloons described herein include polyethylene (PET), flexible polyvinylchloride (PVC) cross-linked polyethylene, non-cross-linked polyolefin, polyurethane, polyetheretherketone (PEEK), silicone, polytetrafluoroethylene (PTFE) or various thermo plastic elastomers. Some embodiments may even employ a thin metal to form the balloons. Some suitable materials for the various flexible elongated members described herein include may include PEEK or silicone. In some embodiments, the balloons and flexible member may be formed of the same materials.

While most applications will employ between 3 and 8 balloons, fingers, legs or segments, a smaller (e.g., 2) or larger number of balloons may be employed. For example, a larger number of balloons may be advantageous where a polymeric stent is to be expanded. As noted above, the above described embodiment may allow for a smaller wall thickness of the balloons over existing designs. Such may allow the expansion structure to be more easily accommodated by the catheter or may advantageously allow for a catheter with a smaller diameter cross-section.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including U.S. provisional patent application Ser. No. 60/985,858 filed Nov. 6, 2007, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A catheter device, comprising:
   a first inflatable balloon;
   a second inflatable balloon;
   at least a third inflatable balloon;
   a catheter having at least one lumen, the catheter physically coupled to move at least the first, the second and the third inflatable balloons through vasculature and the at least one lumen fluidly coupled to an interior of at least one of the first, the second, and the third inflatable balloons;
   wherein
   distal-most end portions of each of the first, the second and the third inflatable balloons are axially moveable with respect to one another; and the first inflatable balloon, the second inflatable balloon and the third inflatable balloon are expandable to collectively provide a circular cross-section and are helically disposed about respective axes that extend generally parallel to one another along the length of the balloons.

2. The catheter device of claim 1 wherein the distal-most end portion of each of at least the first, the second and the third inflatable balloons respectively are axially slideable with respect to one another during at least an initial portion of inflation of at least one of the first, the second and the third inflatable balloons.

3. A medical article, comprising:
a first inflatable balloon; and
at least one second inflatable balloon coupled to at least partially axially overlap the first inflatable balloon, wherein an internal pressure of the second inflatable balloon is equal to an internal pressure of the first inflatable balloon when inflated during use, the first and the second inflatable balloons sized to be received in vivo in a body; wherein
distal-most portions of each of the first and the at least one second inflatable balloon are axially moveable with respect to one another; and
the first inflatable balloon and the second inflatable balloons are expandable to collectively provide a circular cross-section and are helically disposed about respective axes that extend generally parallel to one another along the length of the balloons.

4. The medical article of claim 3 wherein each of at least the first and the second inflatable balloons has a respective port, the ports commonly fluidly coupled.

5. The medical article of claim 4 wherein the first and at least one second inflatable balloons are physically coupled to one another only in their portions adjacent the ports of the first and at least one second inflatable balloons.

6. The medical article of claim 3, further comprising:
a manifold that equally distributes fluid to each of at least the first and the second inflatable balloons during inflation.

7. The medical article of claim 3 in combination with a stent, the medical article further comprising:
a catheter having at least one lumen; and
the first and the at least second inflatable balloons having lengths sufficiently longer than a length of the stent such that the first and the at least one second inflatable balloons physically interact over an entire length of the stent when the first and the at least one second inflatable balloons are inflated and bent, the first and the at least one second inflatable balloons physically coupled to the catheter to move through vasculature therewith, an interior of at least the first and the at least one second inflatable balloons fluidly coupled with the at least one lumen of the catheter.

8. The medical article of claim 7 wherein the first inflatable balloon is longer than the length of the stent by an amount greater than a product of pi times a change in a radial dimension of the first inflatable balloon between an un-inflated state and a maximally inflated state.

9. The medical article of claim 7 wherein the first inflatable balloon is longer than the length of the stent by an amount greater than a sum of a contraction length and a product of pi times a change in a radial dimension of the first inflatable balloon between an un-inflated state and a maximally inflated state.

10. The medical article of claim 3 wherein the first and at least one second inflatable balloons are secured to one another only in one place.

11. The medical article of claim 3 wherein each of the first and at least one second inflatable balloons has a generally wedge-shaped cross section and presents an arcuate outer perimeter when expanded.

12. An in vivo medical article, comprising:
a first structure having a port and a plurality of inflatable chambers formed therein at least two of the inflatable chambers fluidly communicatively coupled to the port, at least two of the inflatable chambers having distal-most portions spaced most distally from the port, at least a portion of the at least two inflatable chambers axially moveable with respect to one another; and wherein
the plurality of inflatable chambers are expandable to collectively provide a circular cross-section and are helically disposed about respective axes that extend generally parallel to one another along the length of the inflatable chambers.

13. The in vivo medical article of claim 12 wherein the distal-most portions of the inflatable chambers are axially movable with respect to one another in response to inflation of at least one of the inflatable chambers from a relatively less inflated state to a relatively more inflated state.

14. The in vivo medical article of claim 12 wherein the first structure includes at least three inflatable chambers.

15. The in vivo medical article of claim 12 wherein the inflatable chambers are slideable with respect to one another in response to inflation of at least one of the inflatable chambers from a relatively less inflated state to a relatively more inflated state.

16. The in vivo medical article of claim 12 wherein the first structure is an inelastic balloon, which is folded in a relatively less inflated state and at least partially unfolded in a relatively more inflated state.

17. The in vivo medical article of claim 12, further comprising:
a catheter having at least one lumen, the catheter physically coupled to the first structure to move the first structure through a bodily lumen and the at least one lumen fluidly coupled to at least one of the inflatable chambers of the first structure.

18. The in vivo medical article of claim 12 wherein an internal pressure of a first one of the inflatable chambers is equal to an internal pressure of a second one of the inflatable chambers when inflated during use.

19. The in vivo medical article of claim 12 in combination with a stent wherein the first structure is a balloon and the inflatable chambers are elongated portions of the balloon, the elongated portions having a length sufficiently longer than a length of the stent to be expanded by the balloon such that the elongated portions physically interact with the stent over an entire length of the stent when the balloon is inflated while bent.

20. The in vivo medical article of claim 12 in combination with a stent wherein the first structure is a balloon and the inflatable chambers are elongated portions of the balloon and the elongated portions of the balloon are longer than the length of the stent by an amount greater than a product of pi times a change in a radial dimension of the inflatable chambers between an un-inflated state and a maximally inflated state.

21. The in vivo medical article of claim 12 in combination with a stent wherein the first structure is an inflatable balloon and the inflatable balloon is longer than the length of the stent by an amount greater than a sum of a contraction length and a product of pi times a change in a radial dimension of the inflatable balloon between an uninflated state and a maximally inflated state.

22. The in vivo medical article of claim 12, wherein the first structure is an inflatable balloon and the inflatable chambers are elongated portions of the balloon and the in vivo medical article further comprises:
 a lubricant carried by at least one of the elongated portions of the balloon to lower a friction coefficient between the elongated portions of the balloon in at least a partially inflated state.

23. The in vivo medical article of claim 22 wherein the elongated portions includes at least one central portion that carries the lubricant and at least two outer portions that are each physically in contact with the central portion and which do not carry the lubricant.

24. The in vivo medical article of claim 22 wherein each of the elongated portions of the balloon carries the lubricant.

* * * * *